US012622592B1

(12) United States Patent
Shoushtarian et al.

(10) Patent No.: US 12,622,592 B1
(45) Date of Patent: May 12, 2026

(54) CHARACTERISING TINNITUS USING FUNCTIONAL NEAR-INFRARED SPECTROSCOPY

(71) Applicant: THE BIONICS INSTITUTE OF AUSTRALIA, East Melbourne (AU)

(72) Inventors: Mehrnaz Shoushtarian, East Melbourne (AU); James Fallon, East Melbourne (AU); Collette McKay, East Melbourne (AU); Shreyasi Datta, East Melbourne (AU)

(73) Assignee: THE BIONICS INSTITUTE OF AUSTRALIA, Fitzroy (AU)

( * ) Notice: Subject to any disclaimer, the term of this patent is extended or adjusted under 35 U.S.C. 154(b) by 59 days.

(21) Appl. No.: 18/024,547

(22) PCT Filed: Sep. 3, 2021

(86) PCT No.: PCT/AU2021/051030
§ 371 (c)(1),
(2) Date: Mar. 3, 2023

(87) PCT Pub. No.: WO2022/047546
PCT Pub. Date: Mar. 10, 2022

(30) Foreign Application Priority Data

Sep. 4, 2020 (AU) ................................ 2020903177

(51) Int. Cl.
*A61B 5/026* (2006.01)
*A61B 5/00* (2006.01)
*A61B 5/12* (2006.01)

(52) U.S. Cl.
CPC ............ *A61B 5/0261* (2013.01); *A61B 5/128* (2013.01); *A61B 5/7267* (2013.01)

(58) Field of Classification Search
CPC ...... A61B 5/0261; A61B 5/128; A61B 5/7267
See application file for complete search history.

(56) References Cited

U.S. PATENT DOCUMENTS

2014/0303424 A1 * 10/2014 Glass ................... A61B 5/4094
600/9
2020/0275872 A1 * 9/2020 Konoshita ............ A61B 5/0075

FOREIGN PATENT DOCUMENTS

KR     10-2019-0064190 A     6/2019
WO     WO-2020018675 A1 *    1/2020 ........... A61B 5/0042

OTHER PUBLICATIONS

Hendrik Santosa et al., "Asymmetry Brain Function in Auditory Cortex: a Functional Near-Infrared Spectroscopy Study," Jul. 2013, IEEE, pp. 1784-1786 (Year: 2013).*
(Continued)

*Primary Examiner* — Michael J Carey
*Assistant Examiner* — Maria Christina Talty
(74) *Attorney, Agent, or Firm* — MARSHALL, GERSTEIN & BORUN LLP

(57) ABSTRACT

Disclosed is a method for characterising tinnitus in a subject using functional near-infrared spectroscopy (fNIRS). The method comprises receiving data comprising fNIRS signals indicative of cortical activity in one or more regions of the subject's brain at a processing device. The received data is processed using the processor device by inputting one or more feature values into a model, where the feature values include one or more features of the received data. The model is configured to provide one or more classification results based on the one or more feature values, the classification results being indicative of at least one characteristic of tinnitus in the subject. Also disclosed is a system for applying the disclosed method.

17 Claims, 24 Drawing Sheets

(56) References Cited

OTHER PUBLICATIONS

A. Rahimpour et al., "Tracking differential activation of primary and supplementary motor cortex across timing tasks: an fNIRS validation study," May 19, 2020, Journal of Neuroscience Methods, pp. 1-9 (Year: 2020).*

Martin Schecklmann et al., "Functional Near-Infrared Spectroscopy to Probe State- and Trait-Like Conditions in Chronic Tinnitus: a Proof-of-Principle Study," Neural Plasticity, 2014, pp. 1-8 (Year: 2014).*

International Search Report and Written Opinion issued in International Patent Application No. PCT/AU2021/051030, dated Nov. 8, 2021.

San Juan et al., "Tinnitus alters resting state functional connectivity (RSFC) in human auditory and non-auditory brain regions as measured by functional near-infrared spectroscopy (fNIRS)", PLoS One, vol. 12(6), e0179150, pp. 1-20, Jun. 12, 2017.

Bahareh Behboodi, "Deep Neural Networks for Assessing Functional Connectivity: an fNIRS Study", Department of Information and Communication Engineering, DGIST, pp. 1-33, Dec. 29, 2017.

Liu et al., "Morphological Neuroimaging Biomarkers for Tinnitus: Evidence Obtained by Applying Machine Learning", Hindawi: Neural Plasticity 2019, vol. 2019, Article ID1712342, pp. 1-11, Dec. 13, 2019.

Santosa et al., "Asymmetry Brain Function in Auditory Cortex: a Functional Near-Infrared Spectroscopy Study", 35th Annual International Conference of the IEEE EMBS Osaka, Japan, pp. 1784-1786, Jul. 3-7, 2013.

Strangman et al., "A Quantitative Comparison of Simultaneous BOLD fMRI and NIRS Recordings during Functional Brain Activation", NeuroImage 2002, vol. 17, pp. 719-731, Dec. 11, 2001.

Chen et al., "Cross Modal Functional Reorganization of Visual and Auditory Cortex in Adult Cochlear Implant Users Identified with fNIRS, " Hindawi: Neural Plasticity, vol. 2016, Article ID 4382656, pp. 1-13, Aug. 20, 2015.

Shoushtarian et al., "Objective measurement of tinnitus using functional near-infrared spectroscopy and machine learning", PLoS One, vol. 15(11), e0241695, pp. 1-20, Nov. 18, 2020.

Extended European Search Report, corresponding European Application No. 21863126.5, mailing date Jul. 19, 2024.

Verma, Rohit et al.: "Functional Near-Infrared Spectroscopy to Probe tDCS-Induced Cortical Functioning Changes in Tinnitus", The Journal of International Advanced Otology, vol. 15, No. 2, Jul. 24, 2019 (Jul. 24, 2019), pp. 321-325, XP093184153, ISSN: 1308-7649, DOI: 10.5152/iao.2019.6022, Retrieved from the internet: URL:http://www.ncbi.nlm.nih.gov/pmc/articles/PMC6750800/pdf/jiao-15-2-321.pdf.

Basura, Gregory J. et al.: "Human central auditory plasticity: a review of functional near-infrared spectroscopy (fNIRS) to measure cochlear implant performance and tinnius perception", Laryngoscope Investigative Otolaryngology, vol. 3, No. 6, Dec. 1, 2018 (Dec. 1, 2018), pp. 463-472, XP091384205, ISSN: 2378-8038, DOI: 10.1002/lio2.185, Retrieved from the internet: URL:http://api.wiley.com/onlinelibrary/tdm/v1/articles/10.1002%2Flio2.185.

Office Action, Japanese patent application No. 2023-514997, mailing date Jan. 13, 2026.

* cited by examiner

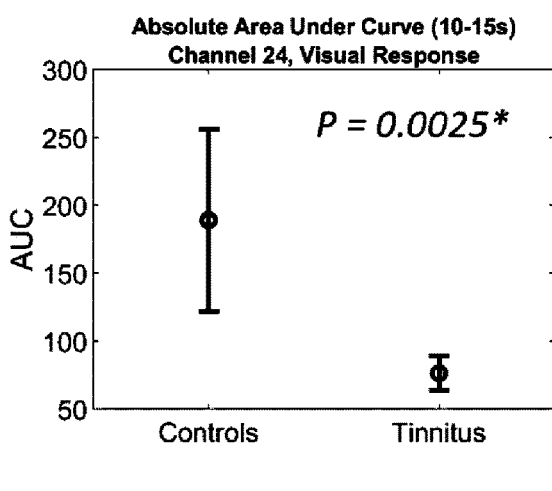
Fig. 16A
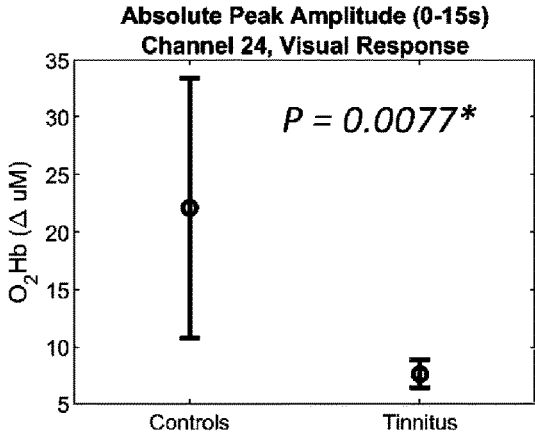
Fig. 16B
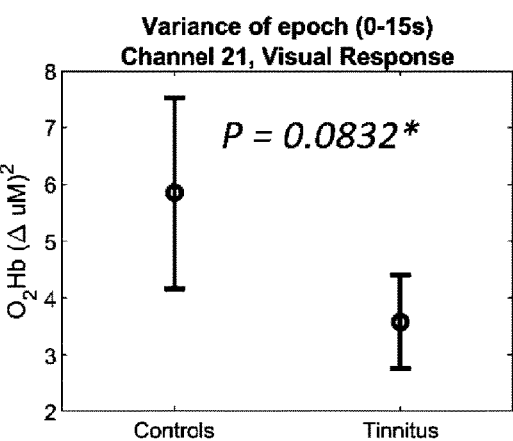
Fig. 16C
Fig. 16D
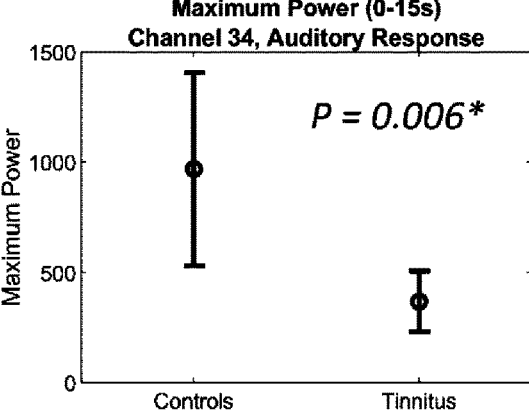
Fig. 16E

CHARACTERISING TINNITUS USING FUNCTIONAL NEAR-INFRARED SPECTROSCOPY

TECHNICAL FIELD

The present disclosure relates to methods and systems for characterisation of tinnitus.

BACKGROUND

Tinnitus is a medical condition characterised by hearing unwanted sounds that are not present externally. Chronic tinnitus is a debilitating condition which affects 6-20% of adults and can severely impact their quality of life. Approximately 20% of adults with tinnitus experience it in a severe form, along with associated symptoms such as depression, cognitive dysfunction and stress.

Despite its wide prevalence, there is currently no clinically used objective test for assessment of tinnitus. In general, clinical assessment of tinnitus relies on subjective feedback from individuals, which may be inaccurate.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each of the appended claims.

SUMMARY

According to one aspect of the present disclosure, there is provided a method for characterising tinnitus in a subject using functional near-infrared spectroscopy (fNIRS), the method comprising:

receiving data at a processor device, the received data comprising fNIRS signals indicative of cortical activity in one or more regions of the subject's brain; and processing the received data using the processor device, the processing comprising:

inputting, into a model, one or more feature values including one or more features of the received data, wherein the model is configured to provide one or more classification results based on the one or more feature values, the one or more classification results being indicative of at least one characteristic of tinnitus in the subject.

Functional near infrared spectroscopy (fNIRS, also known as Optical Tomography) is a non-invasive optical imaging technique, which may be used to measure changes in haemoglobin (Hb) concentrations within cortical regions of the brain. Cortical brain activity may be inferred from these measurements. The fNIRS signals may comprise signals indicative of changes in oxyhaemoglobin ($O_2Hb$) concentration and/or signals indicative of changes in deoxyhaemoglobin (HHb) concentration in the subject's brain.

In some embodiments, the fNIRS signals may be indicative of activity in regions of the subject's brain including one or more of the frontal, left temporal, right temporal and occipital cortical regions. In some embodiments, the regions of the subject's brain include each of the frontal, left temporal, right temporal and occipital cortical regions of the subject's brain.

In some embodiments, the classification results may include a presence or absence of tinnitus in the subject. Additionally or alternatively, the classification results may include a severity rating of tinnitus in the subject. In some embodiments, the severity rating may categorise the tinnitus as either slight to mild tinnitus or moderate to severe tinnitus. In other embodiments, the severity rating may be selected from a greater number of categories. For example, the possible ratings may include slight tinnitus, mild tinnitus, moderate tinnitus and severe tinnitus, or other categories. In some embodiments, the severity rating may be selected from a range of severities. For example, the severity rating may be expressed on a numerical scale.

In some embodiments, the model may further provide a quantification (e.g., as perceived by the subject) of loudness of the tinnitus and/or annoyance produced by the tinnitus. Providing a quantification of loudness and/or annoyance may be useful, for example, in assessing the impact of the tinnitus on the quality of life of the subject. Providing a quantification of loudness and/or annoyance may also be useful in developing of treatments for tinnitus and in defining parameters for assessing the relative success of such treatments.

Feature values may be extracted from the received data using one or more methods. In some embodiments, feature values are extracted from the received data using Information Gain. Information Gain is a measure of entropy in the data, enabling identification of channels and $O_2Hb$/HHb features with the most relevant information for classification. Information Gain may be used, for example, to select the most relevant features by ranking them based on their weight or importance in classification. In other embodiments, alternative features selection methods may be used. For example, the features values may be extracted using one or more of Gini index, SVM (Support Vector Machine) weight, wrapper method, or other suitable methods (for example, different entropy methods).

In some embodiments, the model may comprise an algorithm. In some embodiments, the model may comprise a trained model. The model may have been trained with an artificial intelligence (AI) algorithm based on a previous one or more feature values, for example. The previous one or more feature values may have been mapped to subjective measures of characteristics of tinnitus.

The model may provide classification results using a classification algorithm. The classification algorithm may be selected from the group including, for example, Naïve Bayes; K-nearest neighbour (KNN); Rule Induction; and Artificial Neural Networks (ANN). In other embodiments, alternative classification algorithms, or customised algorithms, may be used.

In some embodiments, the classification algorithm may be multi-level hierarchical classification with binary classifiers at each level. This method of classification may provide advantages compared to a single-level classifier, due to increased flexibility in selecting the most relevant features for each component binary classification module. This method may provide improved classification performance compared to single level multiclass classification.

In some embodiments, the method may further comprise applying a therapy for treating tinnitus and, through the processing of the received data, detecting a change in the one or more characteristics of the tinnitus as a result of applying the therapy. Changes detected as a result of applying therapy may be used to make an assessment of the effectiveness, or otherwise, of the applied therapy.

In some embodiments, the model may be configured to provide a prognostic measure indicative of whether a proposed therapy for treating tinnitus is likely to be effective for treating tinnitus in the subject. As one example, the model may be configured to provide a prognostic measure indicative of whether cochlear implantation would be effective as a treatment for tinnitus in the subject.

In some embodiments, the method may comprise determining a quality of each fNIRS signal and removing signals of inadequate quality prior to the processing of the received data. The quality of each fNIRS signal may be determined based on a level of signal gain, for example. Channels with high gains may be indicative of inadequate detected light intensity. Alternatively, or additionally, the quality of each fNIRS signal may be determined based on a level of cardiac signal content (as indicative of a level of contact between recording optodes of an fNIRS device and the scalp of the subject).

In some embodiments, the fNIRS signals may be subject to pre-processing steps to improve signal quality prior to the processing of the received data. In some embodiments, an algorithm (e.g. a movement reduction algorithm) may be used to detect and remove motion artefacts from the fNIRS signals prior to the processing of the received data. Additionally or alternatively, signals containing movement artefacts in excess of a maximum threshold may be determined to be of inadequate quality and removed prior to processing the received data.

In any aspect herein, the fNIRS signals may comprise a plurality of signals obtained using an fNIRS system that measures a level of cortical activity in the one or more regions of the subject's brain. The fNIRS system may comprise a multi-channel fNIRS system. Each channel may be defined by a source-detector pair. The fNIRS system may comprise a continuous-wave fNIRS system.

In some embodiments, the fNIRS signals may comprise signals from a plurality of channels positioned over each of the respective regions of the subject's brain. In some embodiments, at least one fNIRS signal may be indicative of systemic signals from at least one superficial layer of the subject's head including the scalp and/or the skull. Such systemic signals may be used in pre-processing of the received data, to remove unwanted artefacts or noise, for example.

In some embodiments, the received data may comprise resting-state data. The resting state data may comprise fNIRS signals indicative of cortical activity in two or more regions of the subject's brain while the subject is at rest. In such embodiments, processing the data may further comprise determining at least one resting-state functional connectivity measure between the at least two regions of the subject's brain based on the resting-state data. Resting state functional connectivity is a measure of (or is indicative of) a level of coordination between different neural populations. The one or more feature values may include one or more features of the at least one resting-state functional connectivity measure.

The resting-state data may comprise fNIRS signals obtained during a period in which no stimulus (such as an auditory or visual stimulus) is delivered to the subject, or prior to delivery of any stimulus (such as an auditory or visual stimulus) to the subject. In one example, the resting-state data comprises fNIRS signals obtained over a period of about 6 minutes. In other embodiments, the resting-state data may be obtained over a period having a shorter or a longer duration.

In some embodiments, the resting state functional connectivity measure may be determined from the resting-state data using a Seed Analysis method. The Seed Analysis method may comprise selecting at least one region of the subject's brain as a seed region, and correlating a seed fNIRS signal from the seed region with at least one fNIRS signal from at least one other region of the subject's brain. For example, in some embodiments, a temporal cortex of the subject's brain may be selected as the seed region. In other embodiments, other regions of the subject's brain may be selected as the seed region. The seed fNIRS signal from the seed region may be correlated with at least one fNIRS signal from another region of the subject's brain. For example, the seed fNIRS signal may be correlated with a frontal cortical region, occipital cortical region and/or contralateral temporal region of the subject's brain, or other region of the subject's brain.

In some embodiments, more than one seed region may be selected. For example, seed regions on left and right sides of the subject's brain may be selected in order to determine respective left and right resting state functional connectivity measures. In some such embodiments, both a left and a right temporal cortex of the subject's brain are selected as respective left and right seed regions.

In some embodiments, the seed fNIRS signal may comprise the average of a plurality of fNIRS signals from the seed region. The seed fNIRS signal may be correlated with values obtained for channels in another region of the subject's brain. The correlations with each channel may be assessed individually or averaged (for example, across a region). The correlation may be performed on fNIRS signals comprising $O_2Hb$ concentration measurements and/or fNIRS signals comprising HHb concentration measurements.

In other embodiments, other connectivity analysis methods may be used, additionally or alternatively, to determine the at least one resting-state functional connectivity measure. For example, other time-domain and/or frequency-domain methods of analysing resting state connectivity may be used. As one example, the resting state functional connectivity may be determined using independent component analysis (ICA). ICA allows for analysis of multiple networks in the brain, producing a number of components from the fNIRS signals which are spatially independent. The components can separate resting state networks from each other and from noise. As another example, the resting state functional connectivity measure may be determined using graph connectivity analysis. In graph connectivity analysis, correlations between selected nodes are calculated, the correlations being represented by edges between the nodes. The way nodes are connected and the strength of connections can be compared between groups and between tinnitus patients at different severity levels.

In some embodiments, the received data comprises evoked response data comprising fNIRS signals indicative of cortical activity in at least one region of the subject's brain resulting from at least one stimulus delivered to the subject. The evoked response data may comprise fNIRS signals recorded during delivery of each stimulus. The evoked response data may comprise fNIRS signals recorded during and/or after delivery of the at least one stimulus.

In such embodiments, the one or more feature values may include one or more features of the evoked response data. In some embodiments, the feature values may include one or more amplitudes of the evoked response data. For example, the feature values may include a peak amplitude, an absolute peak amplitude, or a mean amplitude.

Alternatively or additionally, the feature values may include alternative features of the evoked response data. For example, the feature values may include one or more of: a variance, an area under the curve, an absolute area under the curve, a peak power amplitude, an entropy of the waveform;

a temporal content of the waveform; and a spectral content of the waveform. As another example, the feature values may include 'principal components' of the response waveforms, calculated using Principal Component Analysis. In Principal Component Analysis, all the evoked responses to one or more stimuli are considered and the principal components of the responses are calculated. A number of these components (for example, the first ten components, or those covering the majority of the variability in the data) may then be used as feature values. In some cases, the feature value may be determined across a predefined time period. The time period may be, for example, across the duration of the stimulus, across 0-5 seconds after the start of an auditory stimulus, across 10-15 seconds after the start of a visual stimulus, or other time periods as appropriate.

In some embodiments, a general linear model (GLM) may be used to compare the evoked response data to a model of typical hemodynamic response function. From this comparison, a coefficient may be generated which my indicate whether a response is detected. Further, the coefficient may function as a feature value of the evoked response data. Additionally or alternatively, feature values of the evoked response data may be compared to corresponding features of the model hemodynamic response to determine a correlation between the evoked response data and a typical hemodynamic response.

The at least one stimulus may comprise an auditory stimulus. In some embodiments, the auditory stimulus may comprise pink noise. In some embodiments, the auditory stimulus may be provided at a Sound Pressure Level of about 65 dB. Additionally or alternatively, other forms of auditory stimulus may be used.

The at least one stimulus may comprise a visual stimulus. The visual stimulus may be configured to evoke a strong cortical response in the subject. In some embodiments, the visual stimulus may comprise a display of a pattern, e.g., a black and white pattern, such as a checkerboard pattern. The checkerboard pattern may comprise a radial configuration including concentric rings divided into sectors, wherein neighbouring sectors are of opposite colour. The visual stimulus may comprise repeated reversal (or flickering) of the pattern. The reversal of the pattern may be applied at a temporal frequency of about 7.5 Hz (that is, about 15 reversals per second). Additionally or alternatively, other forms of visual stimulus may be used.

In some embodiments, the at least one stimulus may comprise a plurality of discrete stimuli delivered to the subject in a sequence. The at least one stimulus may comprise a plurality of auditory stimuli, a plurality of visual stimuli or a combination of at least one auditory stimulus and at least one visual stimulus. In some embodiments, the method may comprise providing a plurality of auditory stimuli and a plurality of visual stimuli in a sequence. For example, the plurality of auditory stimuli and the plurality of visual stimuli may be provided in an alternating sequence (e.g. alternating one auditory stimuli with one visual stimuli, or alternating one or more auditory stimuli with one or more visual stimuli). Alternatively, the plurality of auditory stimuli and the plurality of visual stimuli may be applied in a different predetermined sequence, or in a substantially randomised order. In some embodiments, the plurality of auditory stimuli and the plurality of visual stimuli may be applied (e.g. pseudo-randomly) so that there is no more than two applications of the same stimulus type (e.g. visual or auditory) in a row.

Each stimulus may have a set duration. For example, in some embodiments, each stimulus may have a duration of about 15 seconds. However, stimuli of other durations may be used. In some embodiments, each stimulus may have a substantially identical duration. In other embodiments, the duration of the stimuli may vary.

Each stimulus may be followed by a rest period in which no stimulus is provided. Each rest period may have a predetermined duration. For example, each rest period may have a duration of between about 20 seconds to about 30 seconds, or more. For example, each rest period may have a duration of about 20 seconds, about 25 seconds, about 30 seconds, or more. In some embodiments, the rest periods may each have a substantially identical duration. In other embodiments, the duration of the rest periods may vary. In some embodiments, the duration of the rest periods may be randomly selected. According to one aspect of the present disclosure, there is provided a non-transitory machine readable storage medium comprising instructions configured to cause a processor device to execute methods according to the present disclosure.

According to another aspect of the present invention, there is provided a system for characterising tinnitus in a subject using functional near infrared spectroscopy (fNIRS), the system comprising:

a processor device, configured to:

receive data, the received data comprising fNIRS signals indicative of cortical activity in one or more regions of the subject's brain; and process the received data, wherein the processing comprises:

inputting, into a model, one or more feature values including one or more features of the received data, wherein the model is configured to provide one or more classification results based on the one or more feature values, the one or more classification results being indicative of at least one characteristic of tinnitus in the subject.

In some embodiments, the received data may comprise resting-state data comprising fNIRS signals indicative of cortical activity in at least one of the subject's brain while the subject is at rest. In such embodiments, processing the data may further comprise determining at least one resting-state functional connectivity measure between the at least two regions of the subject's brain based on the resting-state data. The one or more feature values may include one or more features of the at least one resting-state functional connectivity measure.

In some embodiments, the received data comprises evoked response data comprising fNIRS signals indicative of cortical activity in at least one region of the subject's brain resulting from at least one stimulus delivered to the subject. In such embodiments, the one or more feature values may include one or more features of the evoked response data. In general, the system may be configured to carry out any one or more of the methods steps described in embodiments above, including in relation to pre-processing of the received data, processing of the received data, or otherwise.

The system may further comprise a fNIRS system configured to measure a level of cortical activity in at least two regions of the subject's brain. The fNIRS system may comprise a multi-channel system. For example, the fNIRS system may comprise a plurality of channels configured to be positioned over each of the at least two regions of the subjects brain. In one example, the fNIRS system comprises a plurality of channels configured to be positioned over each of the frontal, left and right temporal and occipital regions of the subject's brain.

The system may further comprise an auditory stimulator configured to deliver an auditory stimulus to the subject. The system may further comprise a visual stimulator configured to deliver a visual stimulus to the subject.

In some embodiments, the system may further comprise a display configured to display the one or more classification results. In some embodiments, the system may further comprise a user input module.

Generally, it will be recognised that the processor device according to embodiments of the present disclosure may comprise one or more processing components for carrying out processing steps according to the present disclosure and may also include one or more storage devices, for storing data such as the resting-state data and/or evoked response data. The processing components and/or storage devices may be at one location or distributed across multiple locations and interconnected by one or more communication links.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

BRIEF DESCRIPTION OF DRAWINGS

By way of example only, embodiments of the present disclosure are now described with reference to the accompanying Figures in which:

FIG. 16A shows a comparison between channel 24 fNIRS data from tinnitus subjects and controls using absolute area under curve over 10-15 seconds as a visual evoked response feature value;

FIG. 16B shows a comparison between channel 11 fNIRS data from tinnitus subjects and controls using mean amplitude over 0-5 seconds as an auditory evoked response feature value;

FIG. 16C shows a comparison between channel 24 fNIRS data from tinnitus subjects and controls using absolute peak amplitude over 0-15 seconds as a visual evoked response feature value;

FIG. 16D shows a comparison between channel 21 fNIRS data from tinnitus subjects and controls using variance of epoch over 0-15 seconds as a visual evoked response feature value; and FIG. 16E shows a comparison between channel 34 fNIRS data from tinnitus subjects and controls using maximum power over 0-15 seconds as an auditory evoked response feature value.

DETAILED DESCRIPTION OF EMBODIMENTS

Methods for characterising tinnitus in a subject using functional near-infrared spectroscopy (fNIRS) according to embodiments of the present disclosure are now described.

Figure 1:
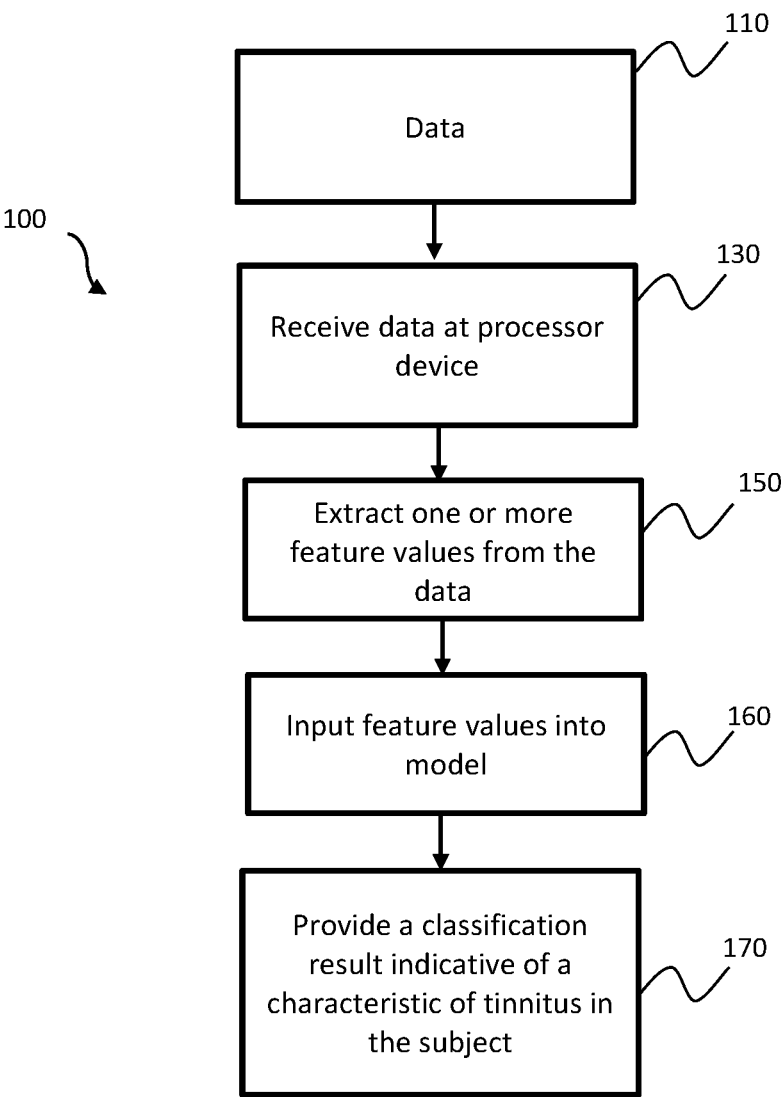
FIG. 1 shows a flowchart of steps in a method of characterising tinnitus in a subject using fNIRS, according to one embodiment of the present disclosure.

Referring to flowchart 100 of FIG. 1, a method of characterising tinnitus in a subject according to an embodiment of the present disclosure is shown. The method comprises receiving data 110 at a processor device 130. The received data 110 comprises fNIRS signals indicative of cortical activity in one or more regions of the subject's brain.

The fNIRS signals may include signals indicative of changes in deoxyhaemoglobin (HHb) concentration and/or oxyhaemoglobin ($O_2Hb$) concentration in cortical regions of the subject's brain. Cortical brain activity in the measured regions may be inferred from these measurements.

The fNIRS signals may be filtered, down-sampled, or otherwise pre-processed. In some embodiments, the fNIRS signals may be pre-processed to remove signals of inadequate quality. For example, the quality of each signal may be determined and signals of inadequate quality removed from the data prior to further processing of the received data. Alternatively, or additionally, undesirable artefacts in the fNIRS signals (due to motion or other interference, for example) may be filtered from the signals prior to further processing of the received data. This is described in further detail in Example 1 below. In other embodiments, for example, embodiments employing AI algorithms, signals of inadequate quality and/or undesirable artefacts may be retained in the signals and the algorithm trained to disregard data from these signals/artefacts.

One or more feature values 150, including one or more features extracted from the received data 110, are then input into a model 160.

The model 160 may comprise a trained model. For example, the model 160 may have been trained with an artificial intelligence (AI) algorithm based on a previous one or more feature values mapped to subjective measures of characteristics of tinnitus. The model 160 may be configured to provide one or more classification results 170 based on the one or more feature values 160, the classification results 170 being indicative of at least one characteristic of tinnitus in the subject. The classification results 170 may include, for example, a presence or absence of tinnitus in the subject, a severity of tinnitus in the subject, a quantification of loudness of the tinnitus and/or a quantification of annoyance produced by the tinnitus. The classification results may be determined using a suitable classification algorithm, for example, Naïve Bayes, K-nearest neighbour (KNN), Rule Induction, Artificial Neural Networks (ANN), or multi-level hierarchical classification.

Figure 2:
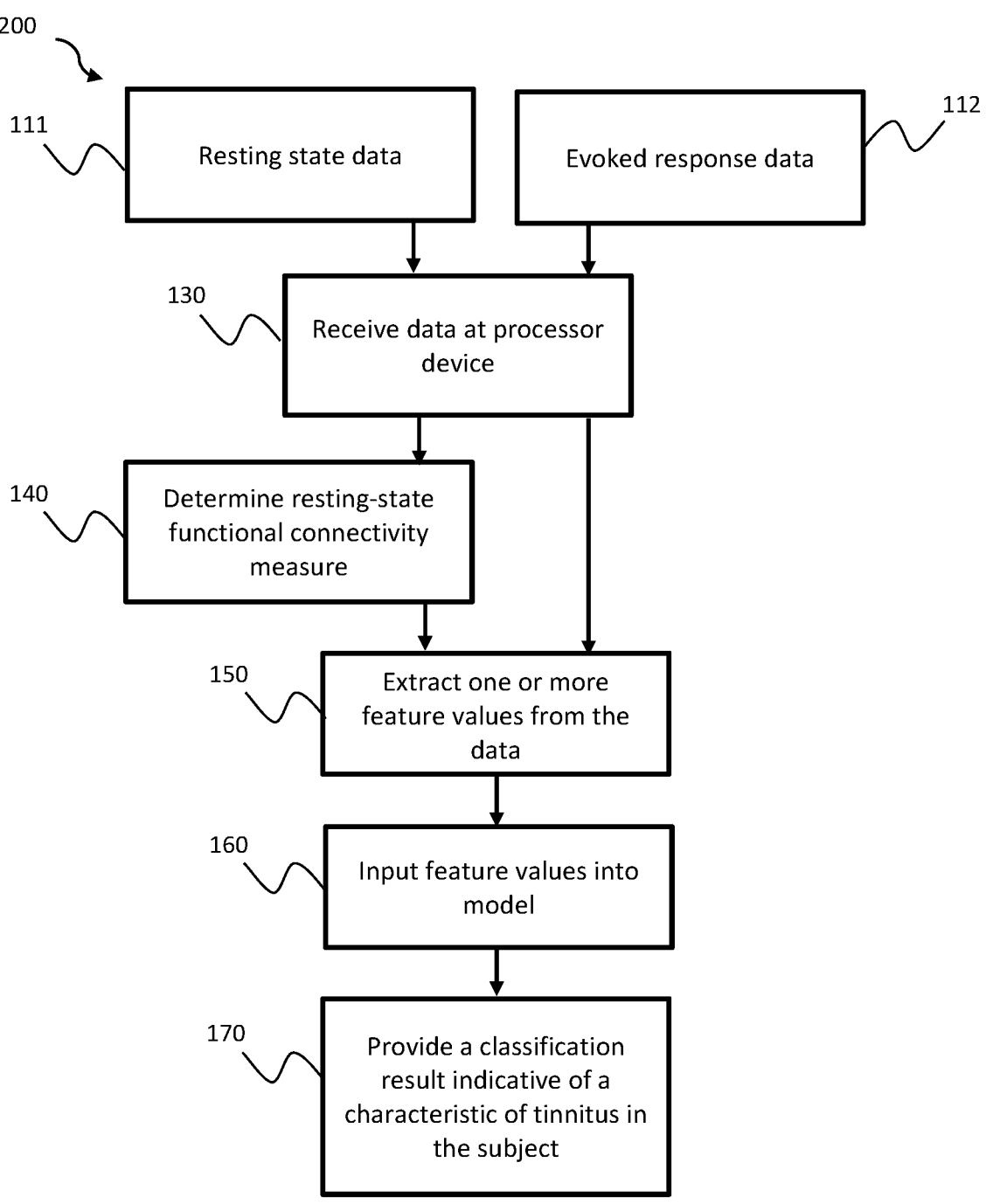
FIG. 2 shows a flowchart of steps in a method of characterising tinnitus in a subject using fNIRS, according to another embodiment of the present disclosure.

As shown in flow chart 200 of FIG. 2, the data may comprise resting state data 111 and/or evoked response data 112, received at the processor device 130.

The resting state data 111 comprises fNIRS signals indicative of cortical activity in two or more regions of the subject's brain, while the subject is at rest. Based on the resting state data 111 (after any pre-processing steps have been applied), at least one resting-state functional connectivity measure 140 is determined between at least two regions of the subject's brain. The measure of resting state functional connectivity 140 may be determined using a Seed Analysis method (described in further detail below), for example, although other methods of determining connectivity may be used as appropriate.

The evoked response data 112 comprises fNIRS signals indicative of cortical activity in at least one region of the subject's brain resulting from at least one stimulus delivered to the subject. The method may comprise steps of delivering at least one stimulus to the subject and recording the evoked response data 112. The evoked response data 112 may correspond to fNIRS signals recorded during and/or after delivery of the stimulus.

The one or more feature values 150 may include one or more features of the resting-state functional connectivity measure 140 and/or one or more features of the evoked response data 112.

The one or more feature values 150 of the evoked response data 112 may include a peak amplitude, an absolute peak amplitude, or a mean amplitude across a predefined time period. Alternatively or additionally, the feature values 150 may include one or more of: a variance, an area under the curve, an absolute area under the curve, a peak power amplitude, an entropy of the waveform; a temporal content of the waveform; a spectral content of the waveform; 'principal components' of the response waveforms (for example, calculated using Principal Component Analysis), or other features of the evoked response data 112. The feature values may be different for auditory and visual evoked response data 112, depending on the model 160 and the classification algorithm used. For example, FIGS. 16A-16E show various examples of comparisons of feature values extracted from fNIRS data from individual channels for auditory or visual evoked response data. In each of the examples shown, the selected combination of feature value and channel is able to demonstrate an overall group difference between the evoked responses of tinnitus subjects and control subjects. The model 320 determine an optimal combination of channels, feature values and classification algorithms to provide the classification results.

In some embodiments the method may be used in the context of applying a therapy for treating tinnitus and detecting any subsequent change in one or more characteristics of the tinnitus as a result of applying the therapy. In some embodiments, the model 160 may be configured to provide a prognostic measure, indicative of whether a proposed therapy for treating tinnitus is likely to be effective for treating tinnitus in the subject. For example, use of the method to derive a prognostic measure for whether cochlear implantation is likely to relieve tinnitus symptoms is outlined in Example 2.

Figure 3:
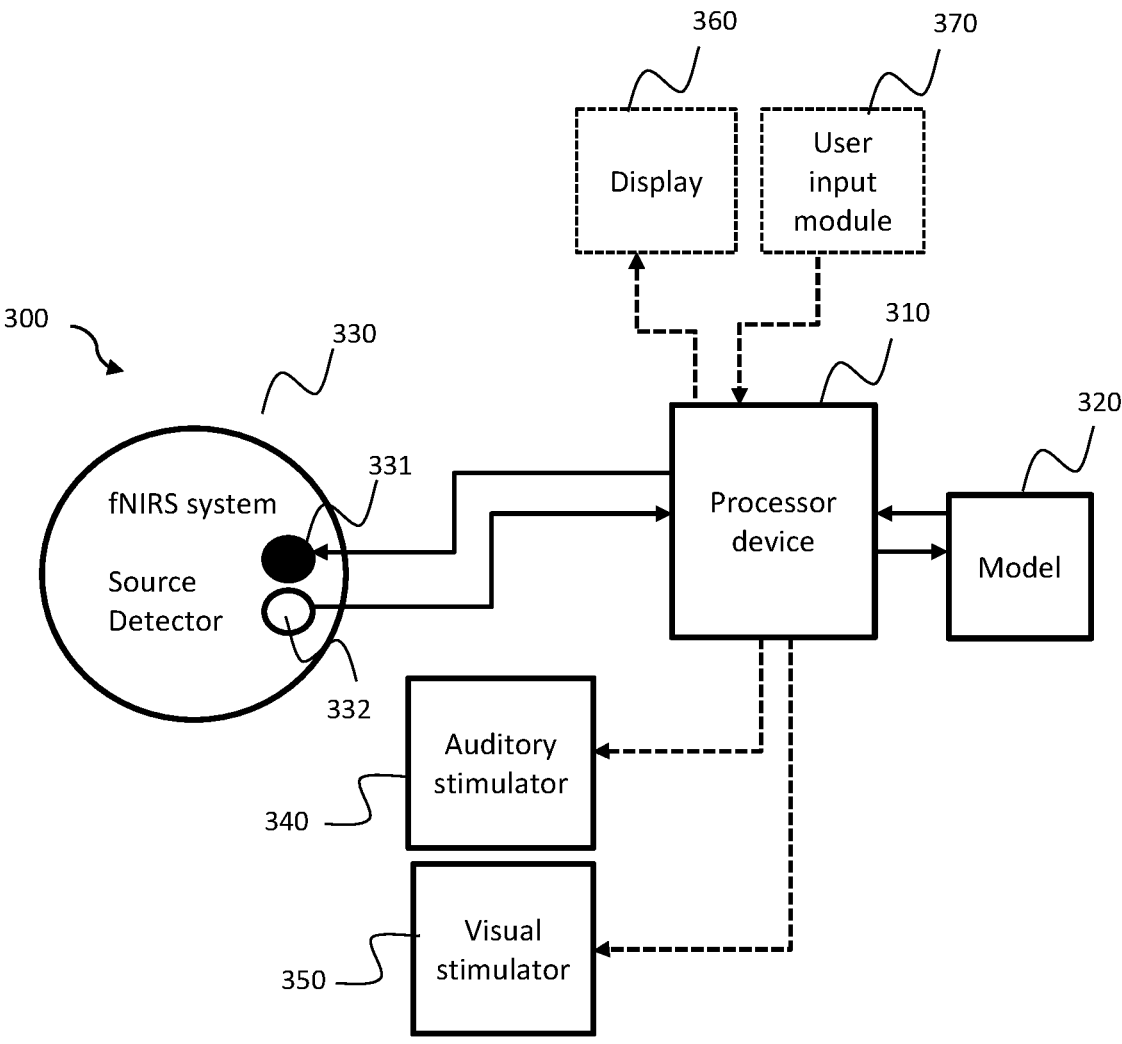
FIG. 3 shows a schematic diagram of a system for characterising tinnitus using fNIRS according to embodiments of the present disclosure.

FIG. 3 shows a schematic diagram of a system for characterising tinnitus in a subject using fNIRS according to embodiments of the present disclosure. The system comprises a processor device 310 which is configured to receive data, including resting-state data and/or evoked response data, comprising fNIRS signals indicative of cortical brain activity in the subject. The processor device 310 is configured to process the resting state data to determine at least one resting-state functional connectivity measure between the at least two regions of the subject's brain based on the resting-state data.

The processor device 310 is further configured to input one or more feature values of at least one resting state functional connectivity measure, and/or one or more feature values of the evoked response data, into a model 320. The model 320 is configured to provide one or more classification results based on the one or more feature values, the one or more classification results being indicative of at least one characteristic of tinnitus in the subject. The model 320 may be a trained model or otherwise. For example, the model 320 may have been trained with an artificial intelligence (AI) algorithm.

Referring again to FIG. 3, the fNIRS signals may be obtained using an fNIRS system 330, where the fNIRS system 330 is configured to measure a level of cortical activity in at least two regions of the subject's brain. The processor device 310 may receive the data comprising fNIRS signals directly from the fNIRS system 330, as shown in FIG. 3. Alternatively, or additionally, fNIRS signal data may be initially received and stored at an intermediate data collection device and later received by the processor device.

Figure 5:
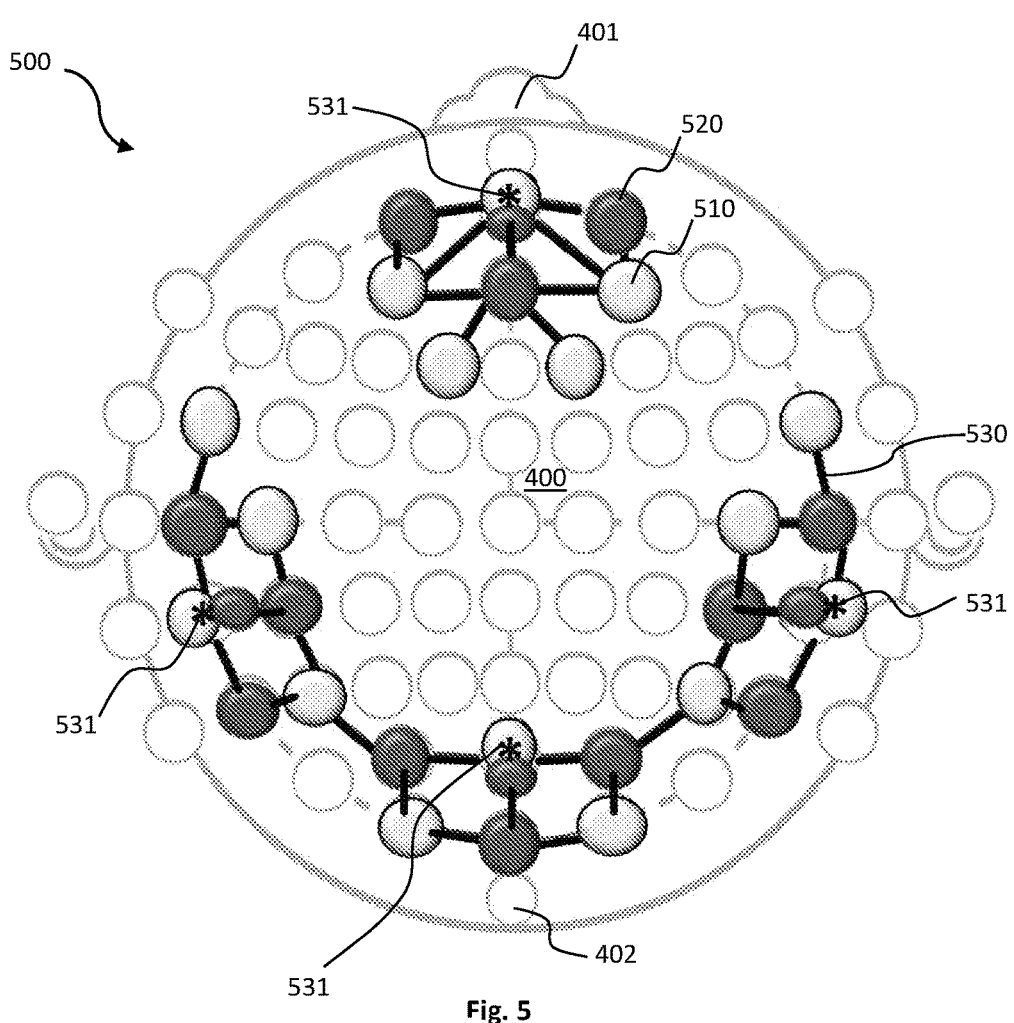
FIG. 5 shows a detail of a source-detector channel layout in a multi-channel fNIRS system in the system of FIG. 3.

The fNIRS system 330 may comprise a multi-channel fNIRS system, wherein each fNIRS channel is defined by a source-detector pair. A single, representative fNIRS channel is illustrated in FIG. 3 by source 331 and detector 332. In some embodiments, the fNIRS system 330 may comprise a plurality of channels configured to be positioned over each respective region of the subject's brain. In one such embodiment, as illustrated in FIG. 5 and discussed in more detail in Example 1 below, the fNIRS system 330 comprises a plurality of channels configured to be positioned over each of the frontal, left and right temporal and occipital regions of the subject's brain.

The processor device 310 may directly or indirectly control the operation of the fNIRS system 330. For example, the processor device 310 may include a light output module for controlling each source 331 of the fNIRS system and a data input module for receiving fNIRS signals from each detector 332 of the fNIRS system 330. Alternatively, the fNIRS system 330 may be controlled by a fNIRS control device, separate from the processor device 310.

In embodiments where the received data includes evoked response data, the system 300 may comprise at least one stimulator for delivering the at least one stimulus to the subject. For example, the at least one stimulus may comprise at least one auditory stimulus and/or at least one visual stimulus. The system may accordingly comprise an auditory stimulator 340 and/or a visual stimulator 350, configured to deliver the respective auditory and/or visual stimuli to the subject.

The auditory stimulator 340 and visual stimulator 350 may be directly or indirectly controlled by the processor device 310, as indicated by the dashed lines in FIG. 3. For example, the processor device 310 may include a sound stimulus output module configured to cause the auditory stimulator 340 to deliver the auditory stimulus and/or a visual stimulus output module configured to cause the visual stimulator 350 to deliver the visual stimulus. Alternatively, the auditory stimulator 340 and/or visual stimulator 350 may be controlled (together or independently) by one or more controllers distinct from the processor device 310, manually, or otherwise.

Optionally, the system 300 may further comprise a display 360. The display 360 may be configured to display the at least one classification result. In some embodiments, the display 360 (or an alternative display) may also be configured to display information related to the operation of the fNIRS system 330. In other embodiments, the visual stimulator 350 may be operable as a display for displaying the at least one classification result and/or information related to the operation of the fNIRS system 330. The system 300 may also comprise one or more user input modules 370 for facilitating user interaction with the system 300.

Example 1

Twenty five subjects with chronic subjective tinnitus (23 experiencing it bilaterally) and twenty-one healthy adults with no history of tinnitus, neurological or hearing disorders were recruited for this study. Data from three healthy subjects were excluded, two due to long hair and poor signal quality and one due to technical issues. Each subject attended one testing session.

Figure 4:
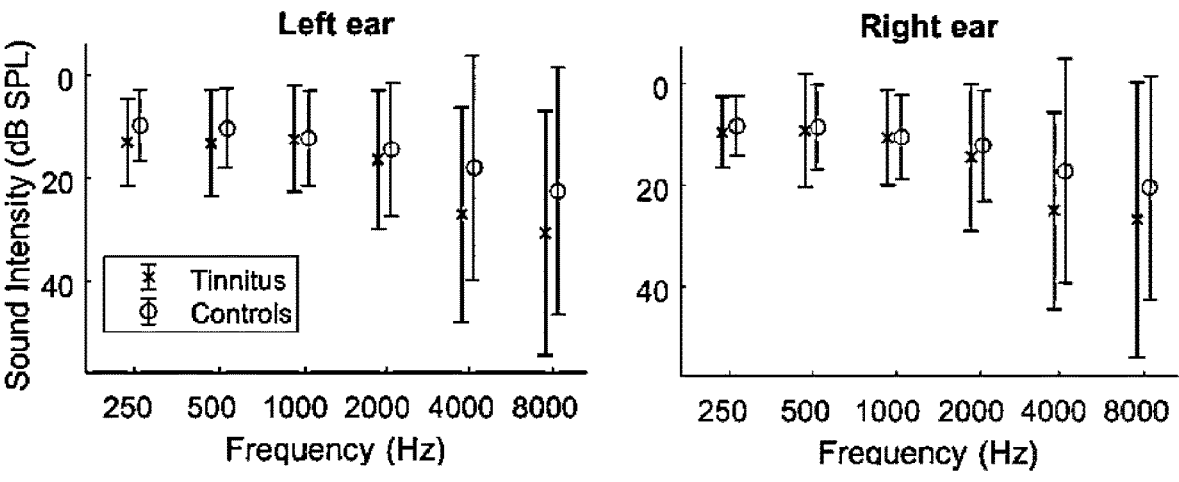
FIG. 4 shows an example of pure tone audiometry testing performed on subjects prior to fNIRS testing.

FIG. 4 shows the results of pure tone audiometry testing which was performed on all subjects at frequencies of 0.25 kHz, 0.5 kHz, 1 kHz, 3 kHz, 4 kHz, 6 kHz and 8 kHz to assess hearing thresholds prior to commencing fNIRS testing. Hearing thresholds averaged across frequencies for each ear were not significantly different between groups. There was no significant difference in mean age between the tinnitus and non-tinnitus subject groups.

Tinnitus severity for each subject was assessed using the Tinnitus Handicap Inventory (THI). The THI is a 25-item test which quantifies the perceived severity of tinnitus on a scale of 0-100. Score ranges are associated with different severity levels (e.g. 0-16 slight tinnitus, 58-76 severe). Participants with tinnitus were also asked to rate the loudness and annoyance of their tinnitus on a scale of 1 to 10 before each recording. Demographic and clinical data are shown in Table 1 below.

TABLE 1

| Participant demographics | | |
|---|---|---|
| | Controls | Tinnitus |
| No. of subjects | 18 | 25 |
| gender (male:female) | 11:7 | 16:9 |
| Age, mean (SD), range | 45.5 (16.7), 25-76 | 48.4 (12.9), 25-68 |
| Handedness | R: 18 | R: 21, L: 2, both: 2 |
| THI, mean (SD), range | N/A | 26.2 (17.1), 4-60 |

TABLE 1-continued

| Participant demographics | | |
|---|---|---|
| | Controls | Tinnitus |
| Tinnitus duration, mean (SD), range | N/A | 11.5 (8.8), 0.5-25 |
| Tinnitus laterality | N/A | R: 2, bilateral: 23 |

THI, Tinnitus Handicap Inventory; R, right; L, left; Tinnitus duration: length of time subjects have experienced tinnitus.

A multi-channel continuous-wave fNIRS system 500 operating at 760 and 850 nm (NIRScout, NIRx Medical Technologies LLC) was used to collect data. FIG. 5 shows a montage of channel locations relative to the subject's head. For each test subject, a total of 16 sources 510 (cross hatched markers) and 16 detectors 520 (black markers) were placed over regions of the subject's head 400 corresponding to frontal, temporal and occipital cortical regions of the subjects brain, by positioning the respective sources 510 and detectors 520 relative to the nasion 401 and inion 402 of the subject's head 400. The white markers indicate potential source/detector positions which were not utilised in this study. Each source 510 to detector 520 pair defines a respective fNIRS channel 530, 531.

The sources 510 and detectors 520 were arranged using NIRSite software (NIRx Medical Technologies LLC) which uses the ICBM-152 head model and allows for export of MNI coordinates corresponding to channel locations. These coordinates were then used in an open-source series of Matlab™ programming and numeric computing platform scripts called the AtlasViewer™ application for the display and anatomical interpretation of fNIRS data to determine the brain region corresponding to each channel location and to ensure the auditory and visual cortex in particular were covered.

The source 510 and detector 520 in most source-detector pairs were positioned 30 mm apart, forming 36 'long' channels 530 (indicated in FIG. 5 by the black connecting lines between sources 510 and detectors 520). In each of the four cortical regions (frontal, left and right temporal and occipital), one 'short' channel 531 (indicated in FIG. 5 by asterisks) was defined by placing a source and detector 11 mm apart. The short channels 531 were configured to detect and record systemic signals from superficial layers of the subject's head (including the scalp and skull) which can interfere with detection of deeper, cortical signals. The recordings from the short channels were used to remove systemic artefacts from the fNIRS signals received from the long channels.

Each channel 530, 531 was assigned an individual number, as follows: frontal region—channel numbers 1, 2, 3, 4, 5, 6, 7, 8, 26, 27, 28, 29; left temporal region—channel numbers 9, 10, 11, 13, 14, 16, 17, 18; right temporal region—channel numbers 30, 31, 32, 34, 35, 37, 38, 39; occipital region—channel numbers 19, 20, 21, 22, 23, 24, 25, 40, 41, 42.

The estimated anatomical regions covered by each of the temporal channels are listed in Table 2, below. The channels over the occipital region covered the cuneus and superior occipital gyrus.

TABLE 2

Anatomical region associated with each temporal channel number

| Left side | | Right side | |
|---|---|---|---|
| Channel no. | Cortical region | Channel no. | Cortical region |
| 9 | Superior temporal gyrus | 30 | Superior temporal gyrus |
| 10 | Superior temporal gyrus | 31 | Heschl's gyrus |
| | | 32 | Supramarginal gyrus |
| 11 | Supramarginal gyrus | 34 | Middle temporal gyrus |
| 13 | Middle temporal gyrus | 35 | Superior temporal gyrus |
| 14 | Middle temporal gyrus | | |
| 16 | Inferior temporal gyrus | 37 | Middle temporal gyrus |
| | | 38 | Angular gyrus |
| 17 | Angular gyrus | 39 | Middle temporal gyrus |
| 18 | Middle temporal gyrus | | |

In this study, features from all long channels 530 were used, allowing the feature extraction algorithm to select the most relevant channels, which for evoked responses were predominantly from the relevant anatomical regions (e.g. auditory response features from auditory channels). However, in other embodiments of the method, fewer channels 530 may be used, which may allow use of a simplified testing setup and/or faster computation times. Alternatively, in some embodiments, a greater number of channels may be used.

A plurality of discrete auditory stimuli were delivered to each subject binaurally via audiometric insert earphones (ER-3A insert earphone, E-A-RTONE™ 165 GOLD, USA) in a sound-insulated booth using Presentation software (Neurobehavioral Systems, USA). Each auditory stimulus consisted of a 15-second segment of pink noise, calibrated using a Norsonic sound level meter (Norsonic SA, Norway) and delivered at 65 dB Sound Pressure Level (SPL). The power in pink noise is inversely proportional to the signal frequency with equal power in different octaves (i.e. doubling of frequencies). This is similar to how the human auditory system perceives sound.

A plurality of visual stimuli were delivered to each subject as a reversing display of circular checkerboard patterns, with pattern reversal at a temporal frequency of 7.5 Hz (15 reversals per second). This pattern produces strong cortical responses in people with good visual acuity. The images were radial in nature and consisted of rings, divided into sectors with neighbouring sectors of opposite colour (black and white).

Figure 6:
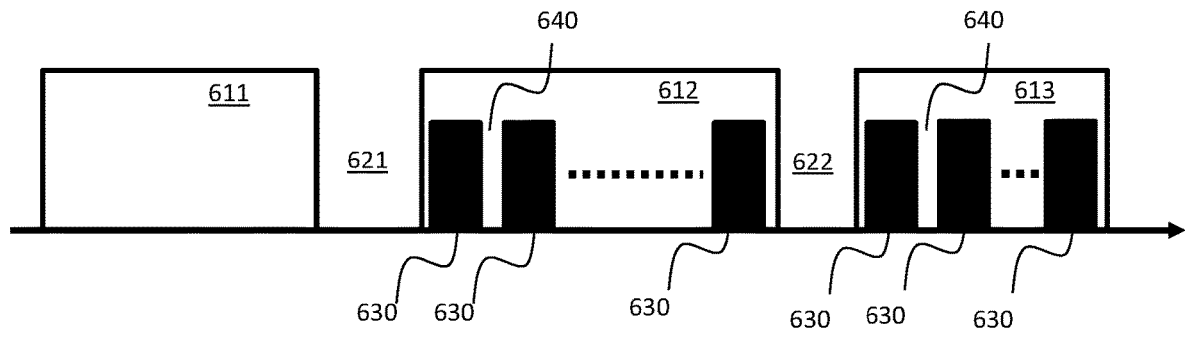
FIG. 6 shows a timeline of an example fNIRS test session used to obtain data according to the method of FIG. 2.

FIG. 6 shows an illustrative timeline of the fNIRS test session. The test session consisted of three recording sessions 611, 612, 613 with short rest breaks 621, 622 given in between. In this example, the rest breaks were of 3-5 minutes duration, although other durations may be used.

The first recording session 611 included a six-minute resting-state recording. During this recording, the subject was instructed to sit still with their eyes closed but not fall asleep. No auditory or visual stimulus was provided to the subject during this session 611.

The second and third recording sessions 612, 613 each included a series of evoked response recordings. In these recording sessions 612, 613, a plurality of 15-second stimuli 630 were delivered to the subject in sequence. In this example, discrete auditory and visual stimuli were delivered in randomised order, with no more than two of the same stimulus type in a row. However, other arrangements of stimuli may be used.

Each stimulus 630 was followed by a non-stimulus interval period 640. In this example, the non-stimulus interval was 20 or 25 seconds, chosen at random. In other embodiments, alternate durations of non-stimulus intervals may be used. In general, the duration of each non-stimulus time period 640 may be selected to allow enough time for any evoked response to subside and the cortical activity to revert to baseline. In FIG. 6, the dotted lines indicate repetition of the pattern of stimulus delivery. In this example, each stimulus type (i.e. auditory or visual) was repeated 10 times in total (six in the second recording and four in the third recording with a break in between the two recordings), although in other examples an alternative number of stimuli may be used. The total recording time (excluding breaks) was approximately 20 minutes.

In this example, the fNIRS data was recorded at a sampling rate of 7.8125 Hz. However, other suitable sampling rates may be used. Data (i.e., from fNIRS signals) was recorded continuously during each recording session. For the evoked response recording sessions 612, 613, the continuous data recording was later correlated with the time of delivery of each of the stimuli 630 to extract portions of the data corresponding to each evoked response.

Data processing was performed in Matlab™ 2019a (Mathworks™, USA). Pre-processing of fNIRS signals was performed using "NIRS Brain AnalyzIR" Toolbox and custom written Matlab™ scripts. Channels with poor signal quality were selected using the following criteria and excluded from further analysis. First, channels with gains over 7 showing inadequate detected light intensity were rejected. The gain was calculated by the NIRx device during a calibration procedure performed prior to each experiment. Channels were also checked for their cardiac signal content using a scalp coupling index (SCI), which was calculated by band-pass filtering the two detected signals at 760 and 850 nm between 0.2 to 2.5 Hz (22). This provides an indication of the degree of contact between optodes (detectors) and the scalp. Signals from optodes with good skin contact will mainly contain heart rate data and hence be highly correlated. Channels with SCI values less than 0.75 were rejected. On average, 13% of channels were rejected.

For the remaining channels the following pre-processing steps were applied. For resting state recordings, the original unfiltered signals from each channel were down-sampled to 1 Hz and converted to optical density. For evoked response recordings, conversion to optical density was performed at the original sampling rate. Short channel correction was applied to optical density data using the function ntbxSSR.m in the NIRS toolbox (parameter task set to 0). The corrected optical density in each long channel was calculated by subtracting a fraction of the closest short channel. This subtraction removed two sources of interference: fluctuations measured from the scalp; and global fluctuations such as systemic responses and respiration. Concentration changes of oxygenated and de-oxygenated haemoglobin ($O_2Hb$ and HHb respectively) were then estimated using the modified Beer-Lambert law.

A seed analysis method was used to investigate resting-state functional connectivity. In seed analysis, a cortical region is selected as the seed and its connectivity with other regions is examined by finding correlations between the seed region and the other brain regions. This example utilised two channels over the temporal cortex on each side of the head as seed channels. Channels 9 and 10 on the left side and 30 and 31 on the right, were estimated to cover the superior temporal and Heschl's gyrus (as set out in Table 2). On each side, signals from the two channels were then averaged and used as respective left and right seeds. Correlations between seed channels and the other channels were calculated using whitened correlations (NIRS toolbox function nirs.sFC.ar-_corr.m) (27). This is a robust correlation method, which addresses the sensitivity of fNIRS to false correlations due to the slow hemodynamic signal, systemic physiological noise such as heart rate and breathing (serial correlations) and motion artefacts which can introduce non-normal noise structures. Values obtained for channels comprising frontal and occipital regions of interest (ROI) were then averaged for statistical analysis. The frontal ROI included channels over the superior frontal gyrus, medial, superior frontal gyrus, medial orbital and middle frontal gyrus (channels 1, 3, 4, 5, 6, 7, 8, 26, 27, 28, 29). The occipital ROI chosen covered the cuneus and superior occipital gyrus (channels 20, 21, 23, 24, 25, 41, 42). Whitened correlations were derived from both $O_2Hb$ and HHb signals and compared between groups.

To analyse evoked responses, motion artefacts were removed using the function "WaveletFilter" (outlier threshold set to 3). Signals were band-pass filtered between 0.01-0.12 Hz by applying zero-phase $8^{th}$ order Butterworth high-pass (at 0.01 Hz) and low-pass (0.12 Hz) filters respectively. $O_2Hb$ and HHb concentrations were then estimated using the modified Beer-Lambert law. For each channel, $O_2Hb$ and HHb signals were epoched from t=−5 to t=30 seconds relative to stimulus onset using the "EpochExtraction" function which removes linear trends and baseline corrects epochs by subtracting the baseline mean. Based on an outlier detection function, epochs with amplitudes exceeding 2.5 standard deviations above the epoch mean were rejected. For each of the conditions recording auditory and visual responses, mean $O_2Hb$ and HHb activation across time windows 0 to 5 seconds (for auditory responses) and 10-15 seconds (visual) were calculated. For statistical analysis, visual evoked responses were averaged over occipital channels and auditory responses were averaged separately over the left and right temporal channels.

To combine features from resting state and evoked response signals from fNIRS channels over different cortical regions, machine learning methods including feature selection and classifiers were used. Features input to these algorithms included auditory and visual response amplitudes and frontal and occipital connectivity measures described above. Here, features from all channels were used as individual inputs (and not averaged over ROIs) to allow the feature selection algorithms to automatically select channels which would best distinguish between groups. Both $O_2Hb$ and HHb-derived features were used. Information Gain was used to select the most relevant features by ranking them based on their weight or importance in classification. Information Gain is a measure of entropy in the data and enables identification of channels and/or $O_2Hb$/HHb features with the most relevant information for classification.

The selected features were then used with four different classification methods to classify subjects as controls or experiencing tinnitus. Classifiers were also used to differentiate the subjects based on tinnitus severity. The subjects were classified as having slight/mild versus moderate/severe tinnitus (based on THI ratings). In the latter analysis data was categorised into two groups only, to increase the sample size in each, however in other examples more categories may be used. For example, the severity classification may include slight, mild, moderate, and severe tinnitus as distinct ratings. In other examples, further severity ratings may be used to classify the subjects into a larger number of groups.

The four classifiers assessed were Naïve Bayes, K-nearest neighbor (KNN), Rule Induction and Artificial neural networks (ANN). In other examples, other suitable classification algorithms may be used, for example, multi-level hierarchical classification. To assess the performance of these algorithms, 10-fold cross validation was used. This validation method randomly partitioned the dataset into 10 subsets. One subset was kept for testing while the other nine were used for training. This process was iterated throughout the whole 10 subsets (each time using one of the 10 subsets for testing) and the average sensitivity (true positive rate), specificity (true negative rate) and accuracy of the classifier were calculated. Classification accuracy or predictive performance was calculated as the number of correctly predicted samples over the total number of samples.

Figure 7:
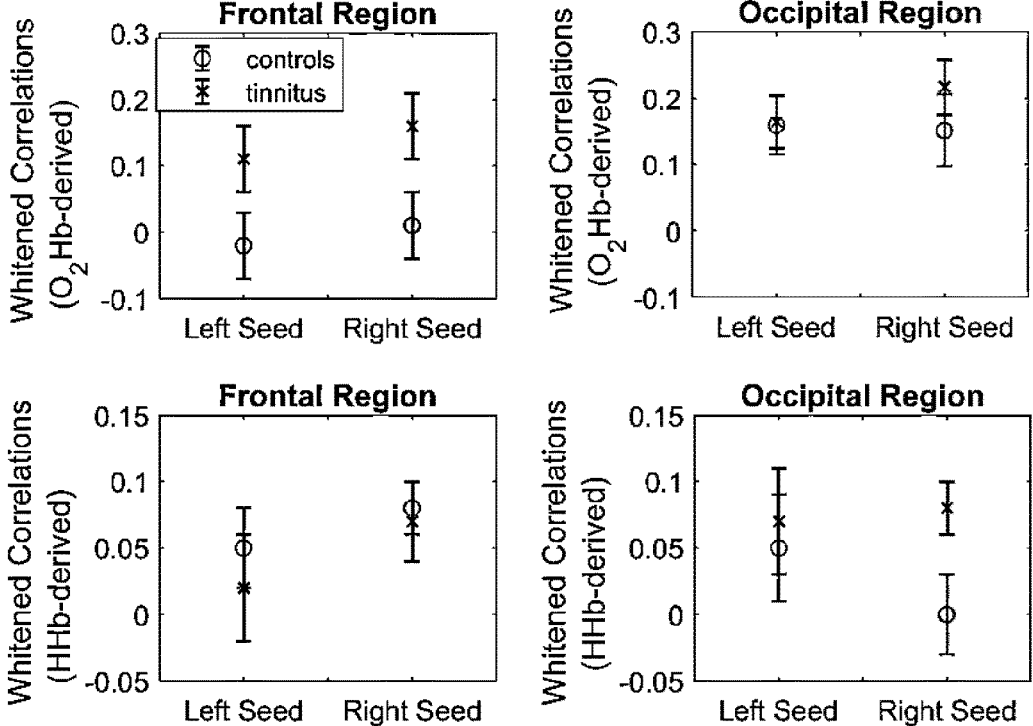
FIG. 7 shows a comparison of measures of resting state functional connectivity between temporal seeds with frontal and occipital channels.
Figure 8A:
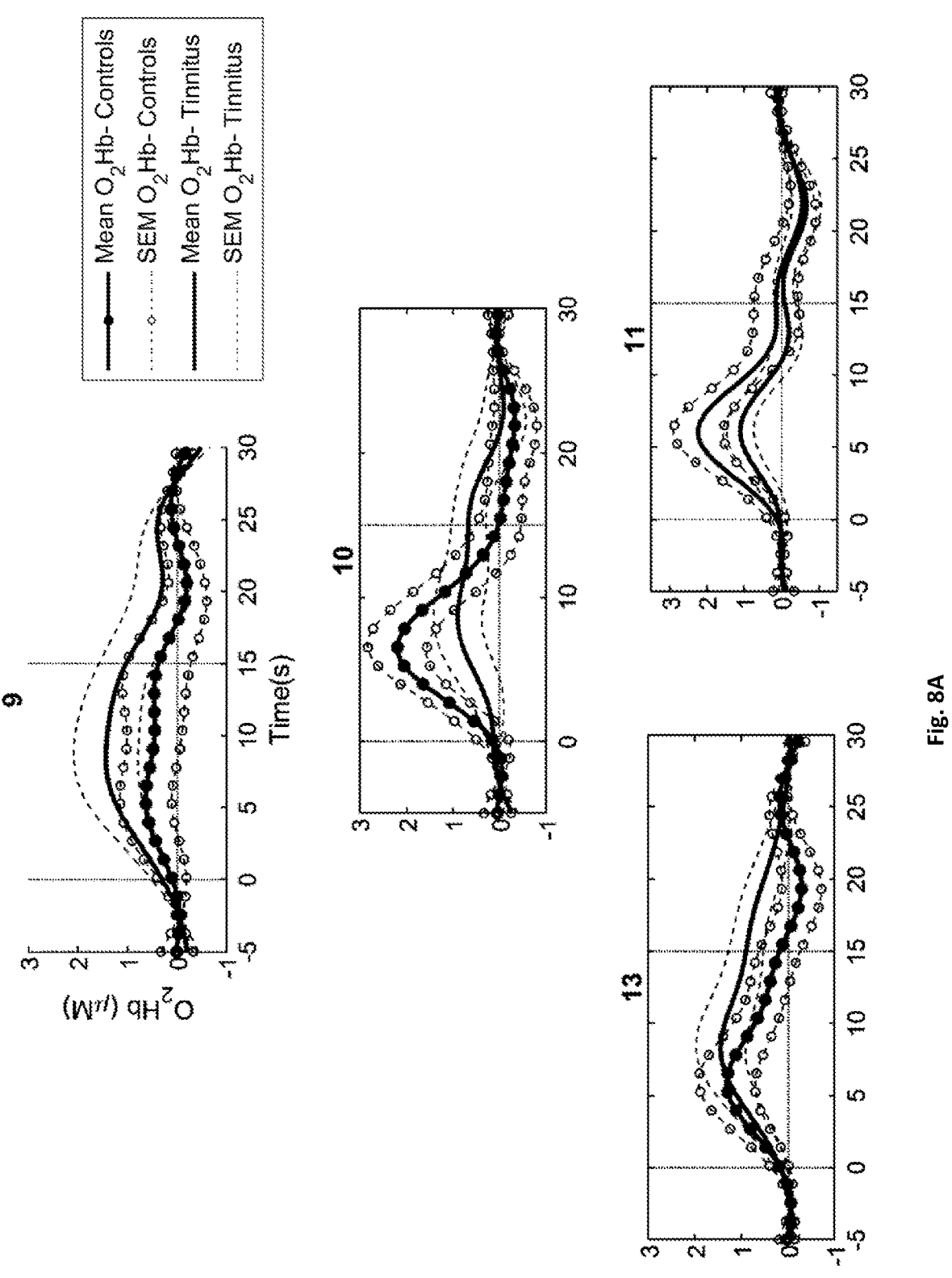
FIGS. 8A to 8B show group averaged $O_2Hb$ fNIRS auditory evoked responses recorded from channels over the left and right temporal cortex, respectively.
Figure 8A:
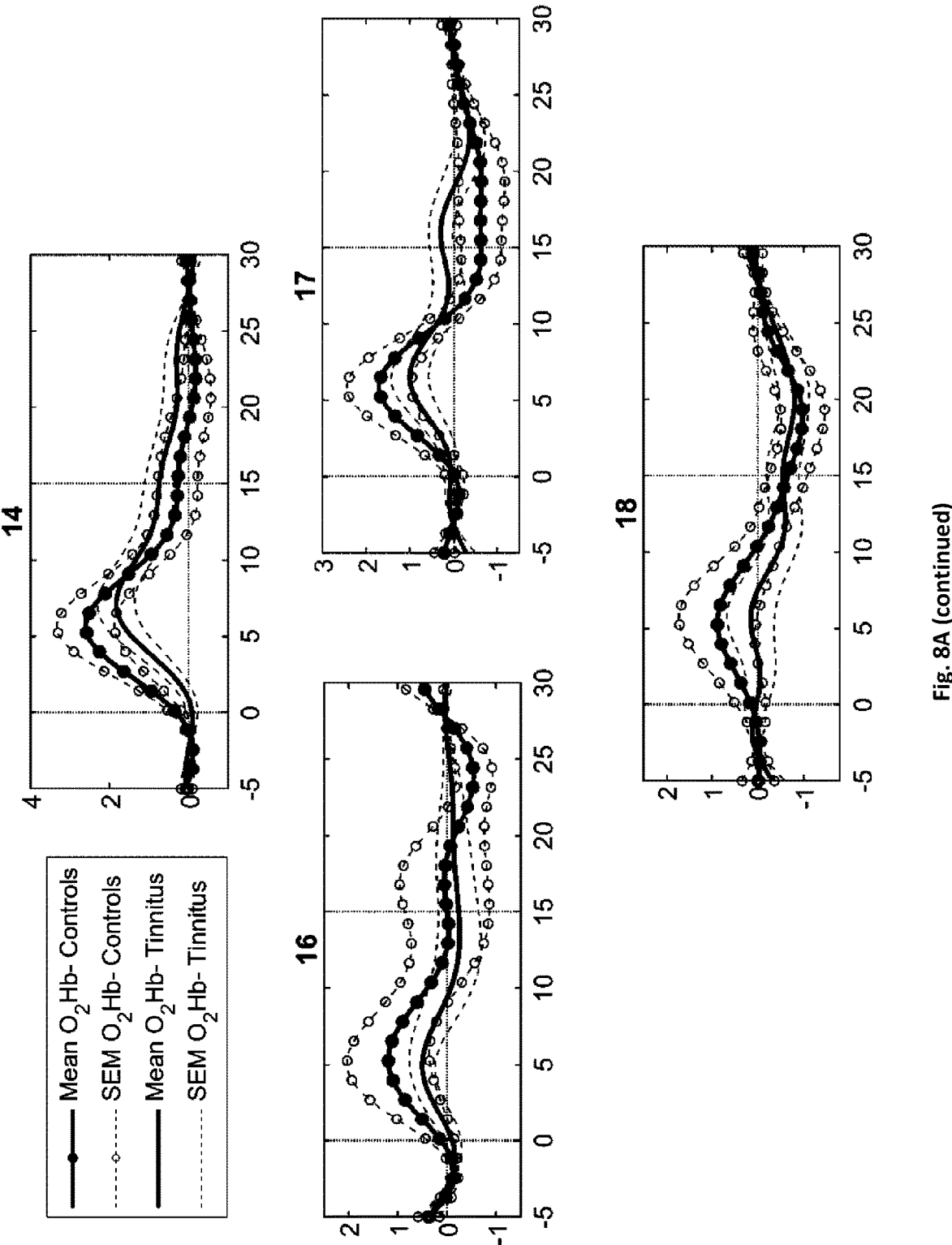
Figure 8B:
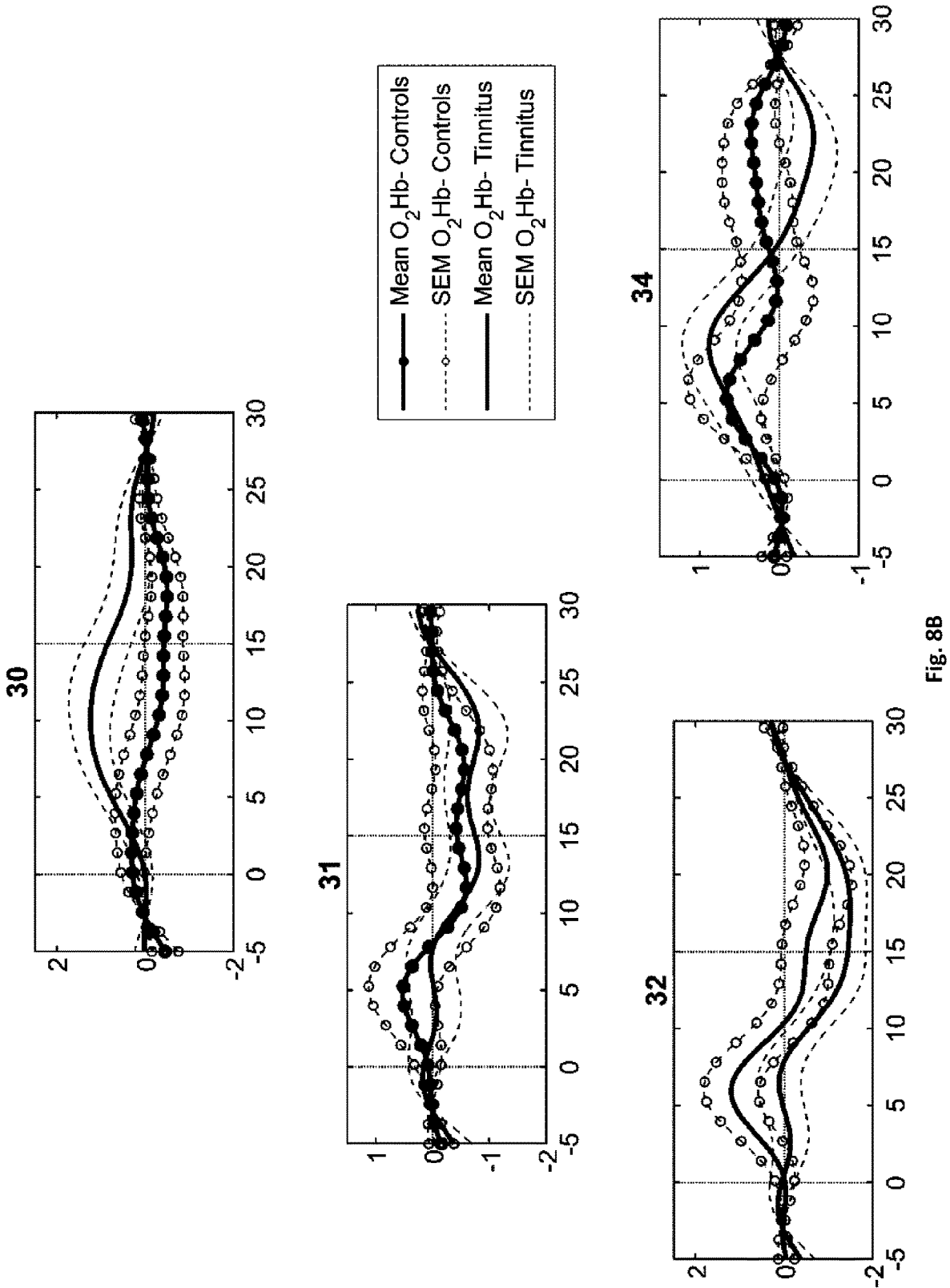
Figure 8B:
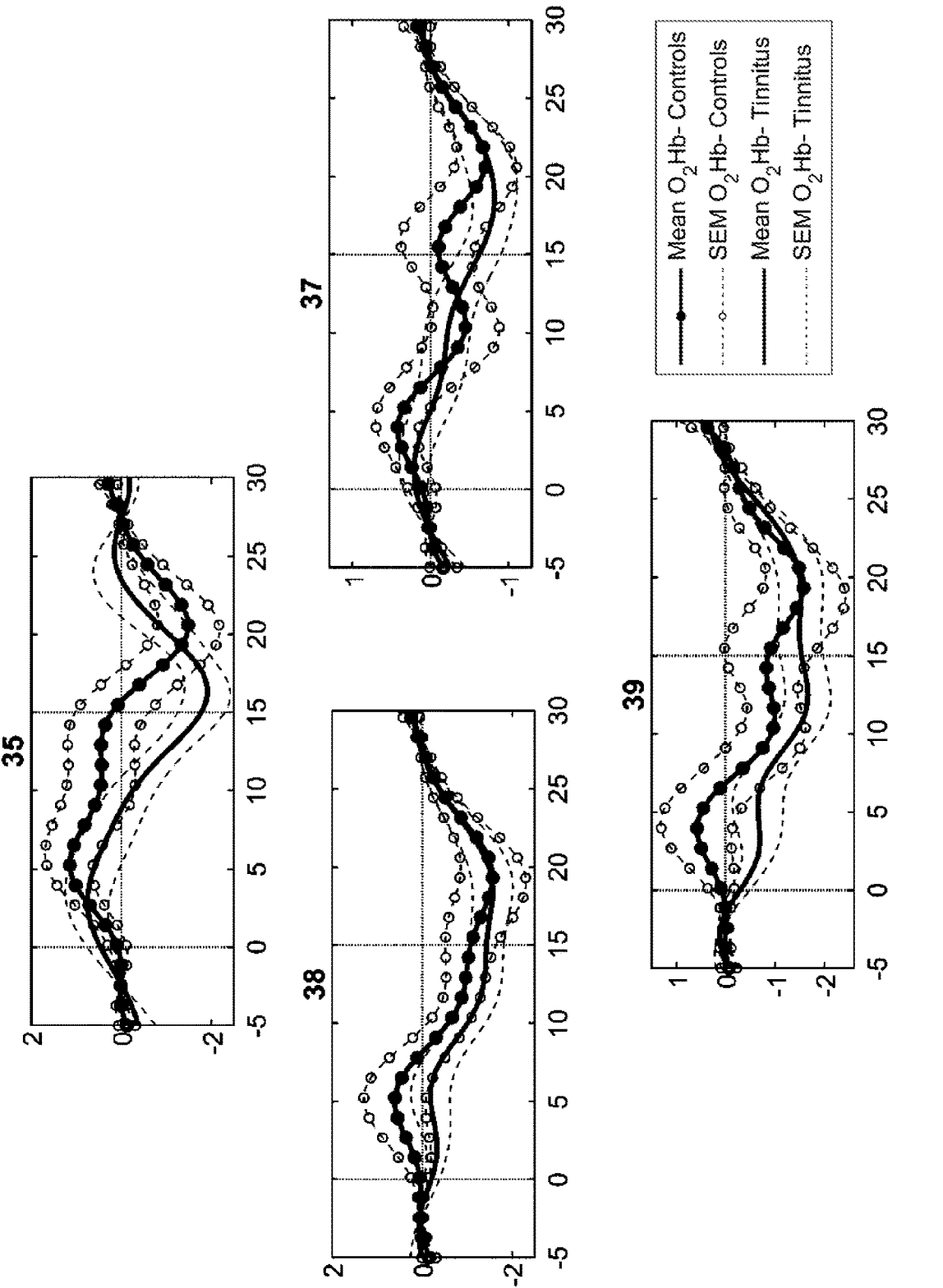
Figure 8C:
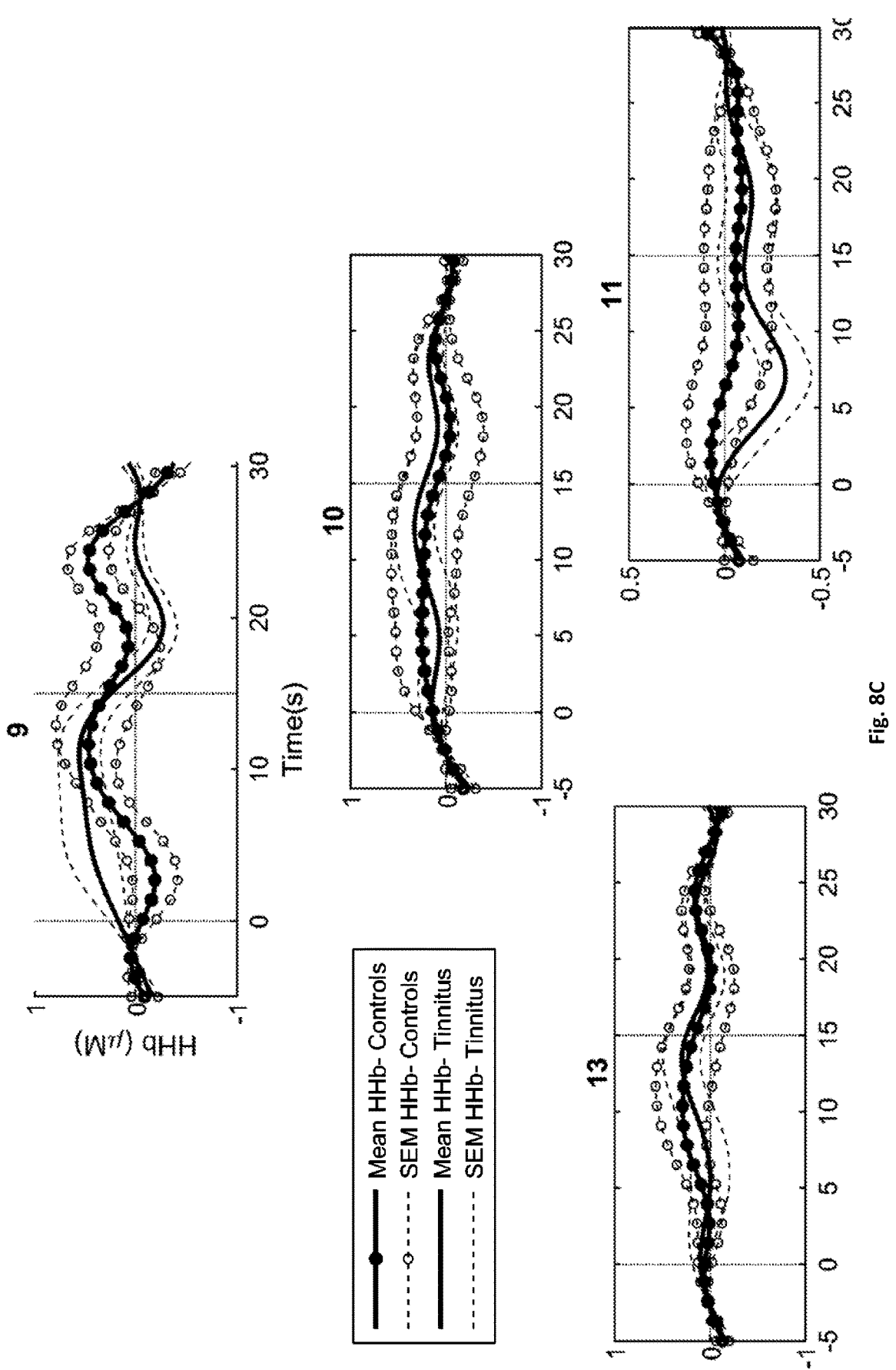
FIGS. 8C to 8D show group averaged HHb fNIRS auditory evoked responses recorded from channels over the left and right temporal cortex, respectively.
Figure 8C:
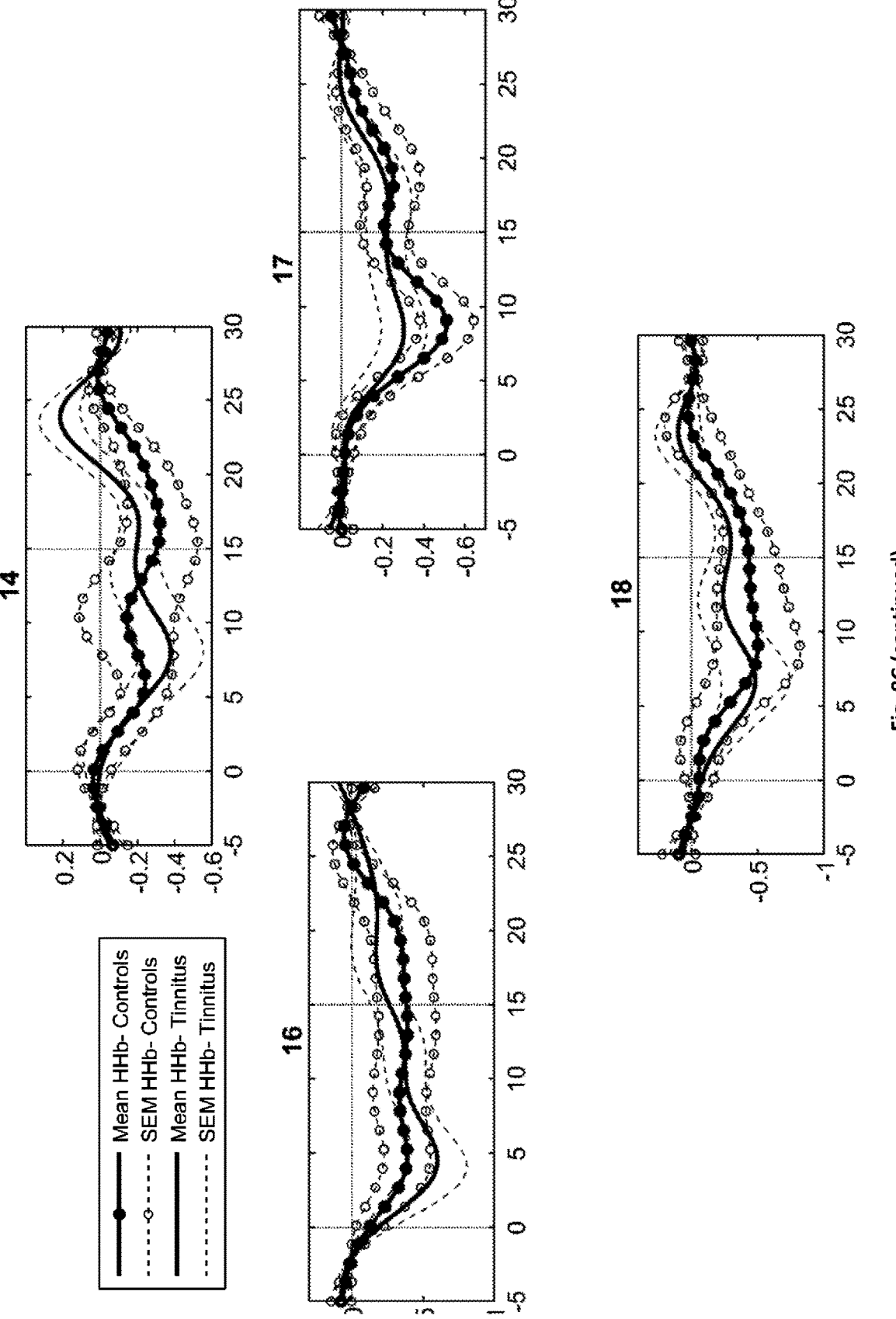
Figure 8D:
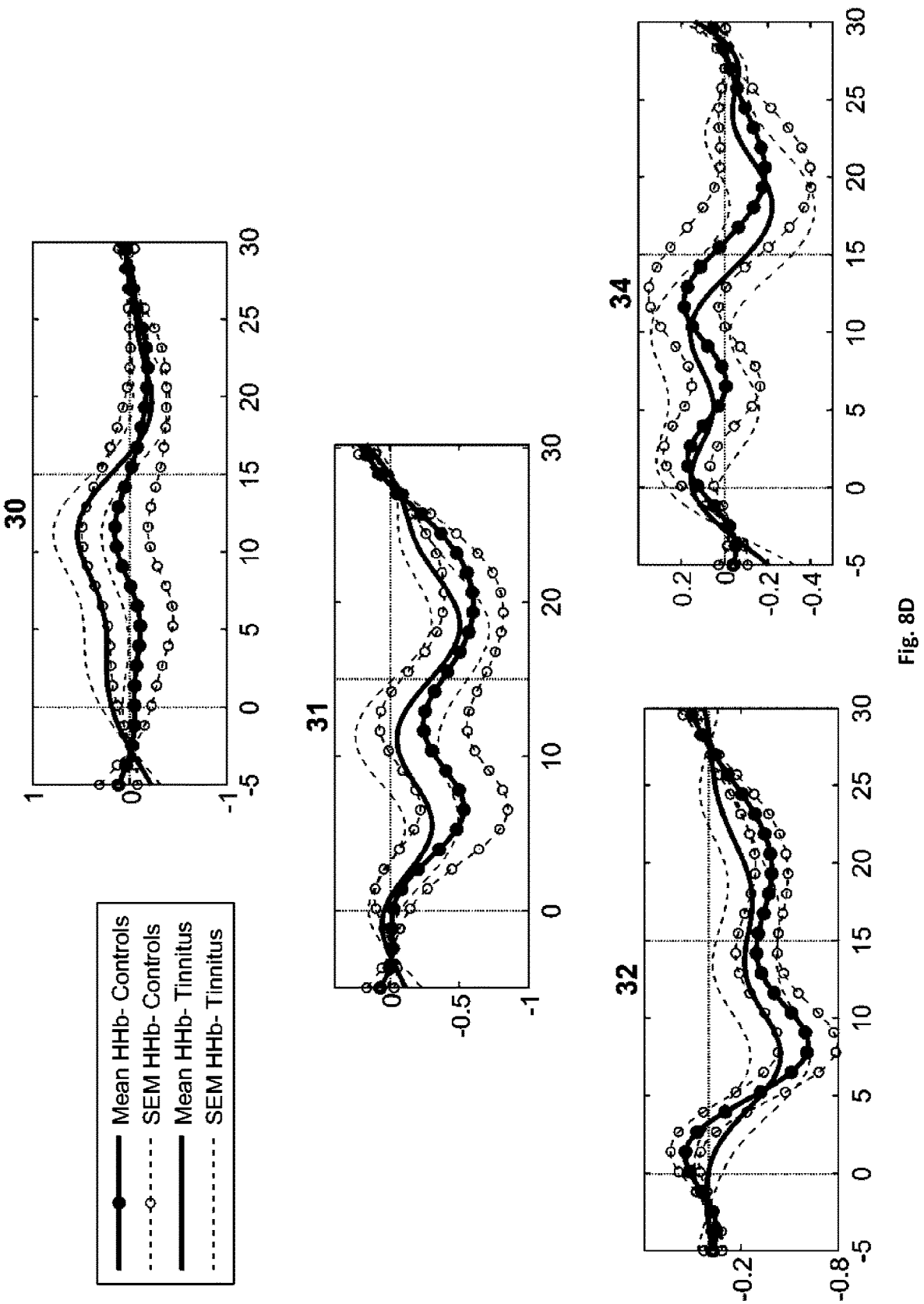
Figure 8D:
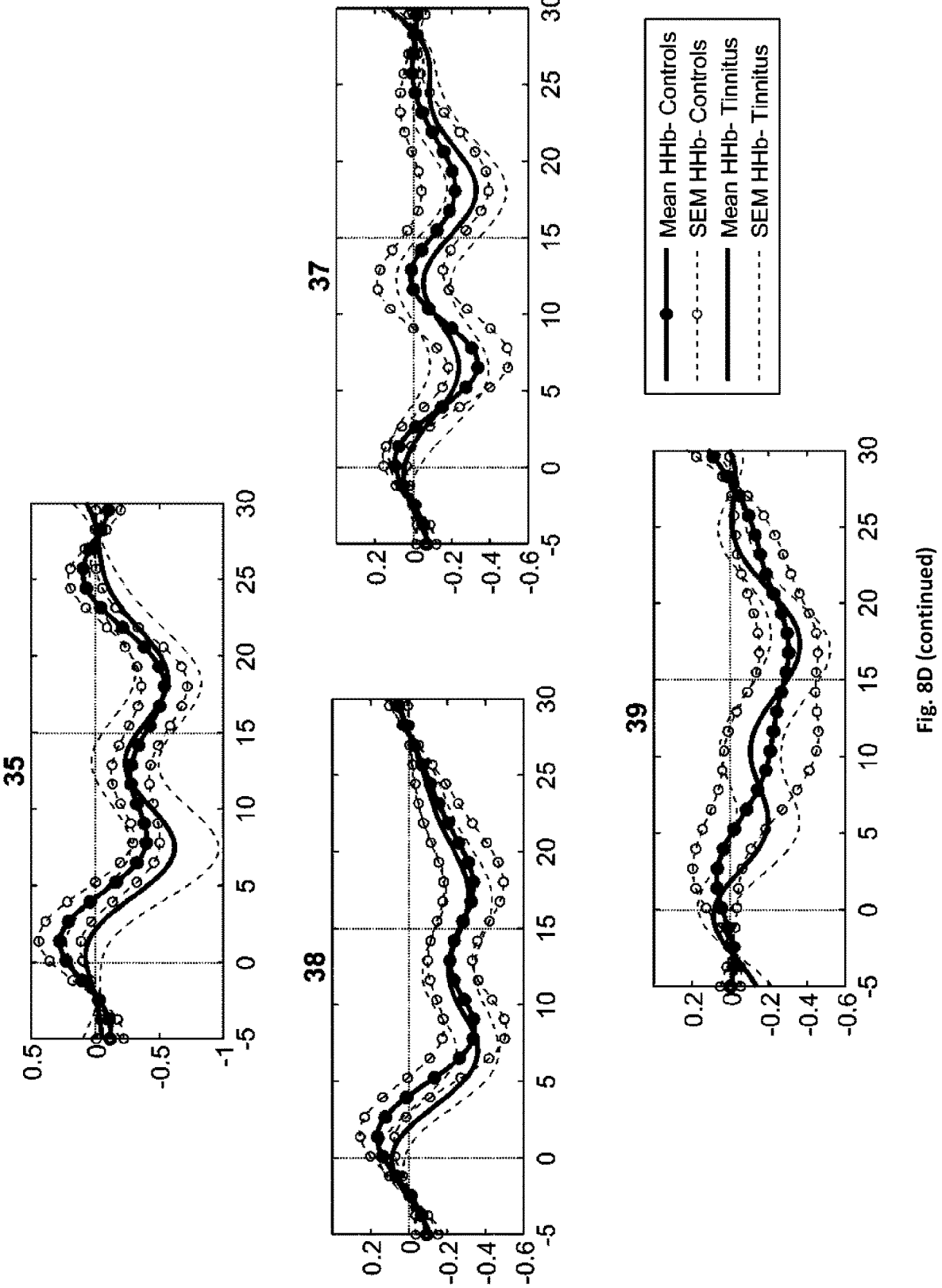

FIG. 7 shows the differences between measures of connectivity between temporal seeds with frontal and occipital channels. Connectivity measures between both left and right seeds with frontal $O_2Hb$ signals were higher in the tinnitus group, with right seed differences reaching significance. Right seed occipital connectivity values derived from HHb signals were significantly higher in the tinnitus group. This was not found for left seed connectivity.

FIGS. 8A to 8D show group averaged $O_2Hb$ auditory evoked responses recorded from channels over the left and right temporal cortex. FIGS. 8E to 8H show group averaged HHb auditory evoked responses recorded from channels over the left and right temporal cortex. The channel numbers are shown above each graph. The dashed vertical lines show stimulus onset and offset times at 0 and 15 seconds. Auditory response amplitudes were averaged over the first five seconds following stimulus onset and compared between left and right auditory regions using paired t-tests and between groups using independent sample t-tests. This period was chosen to capture rise time or onset of the response which lasts on average 5 seconds. There was no significant difference between left and right auditory responses. Averaged across both sides, the auditory response was smaller in the tinnitus group. This group difference was not found for HHb responses.

Figure 9A:
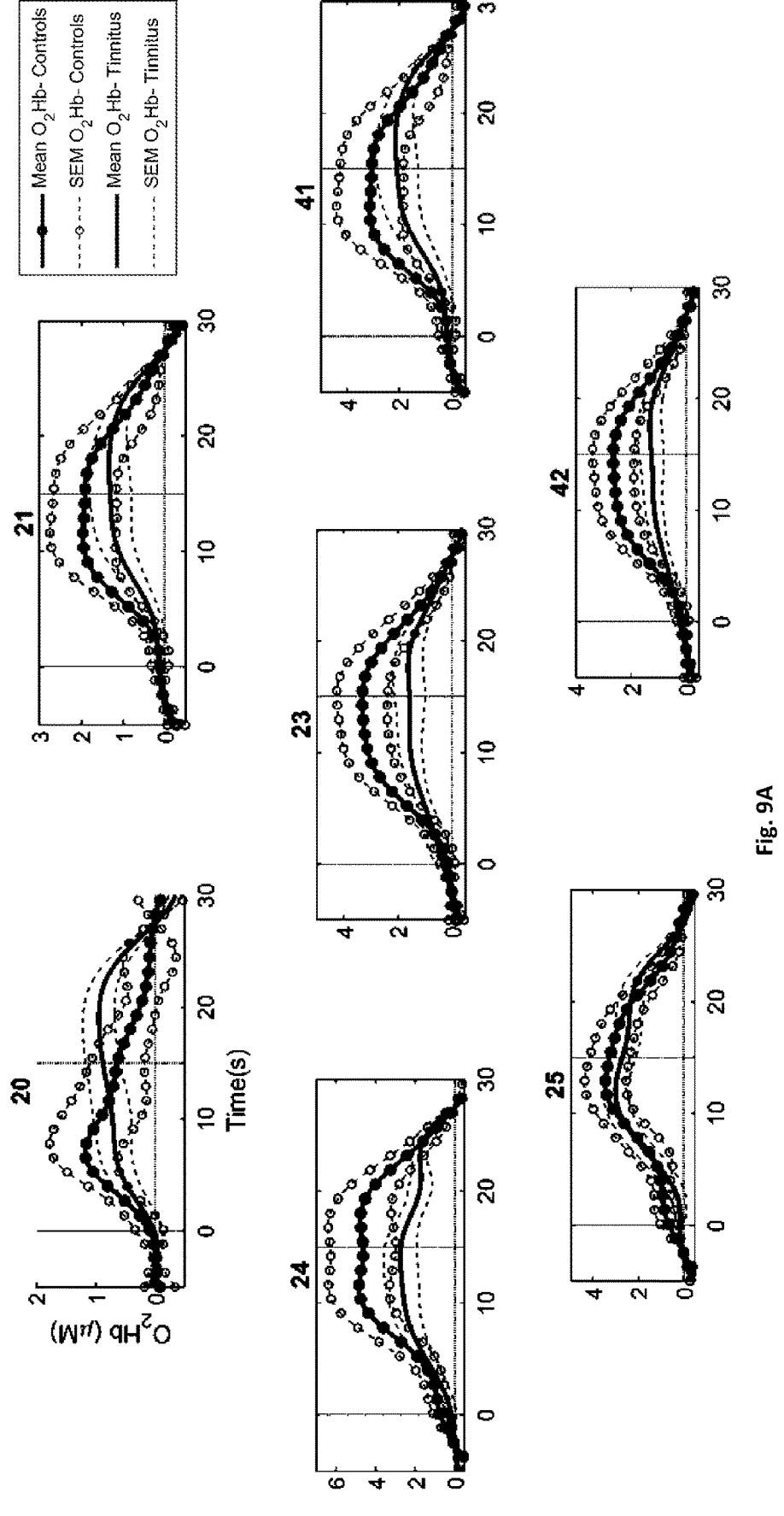
FIGS. 9A and 9B show $O_2Hb$ and HHb visual evoked responses, respectively, recorded from occipital channels over the cuneus and superior occipital gyrus.
Figure 9B:
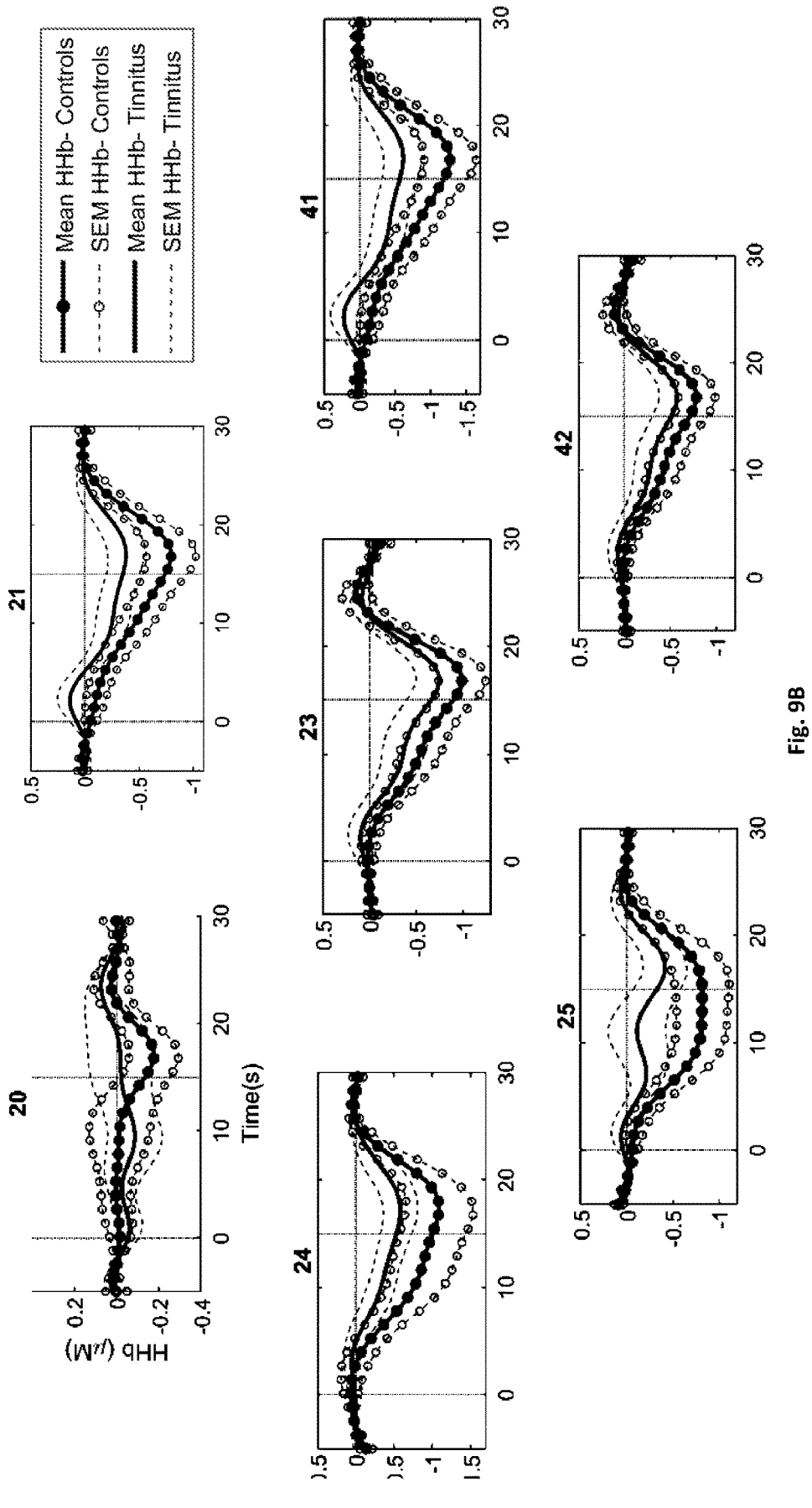

FIGS. 9A and 9B show $O_2Hb$ and HHb visual evoked responses, respectively, recorded from occipital channels over the cuneus and superior occipital gyrus. The channel numbers are shown above each graph. Vertical lines show stimulus onset and offset times at 0 and 15 seconds. The visual response was more sustained in duration following stimulus onset compared to the auditory response. Response amplitudes averaged over 10-15 seconds following stimulus onset were significantly larger in the control group.

Figure 10A:
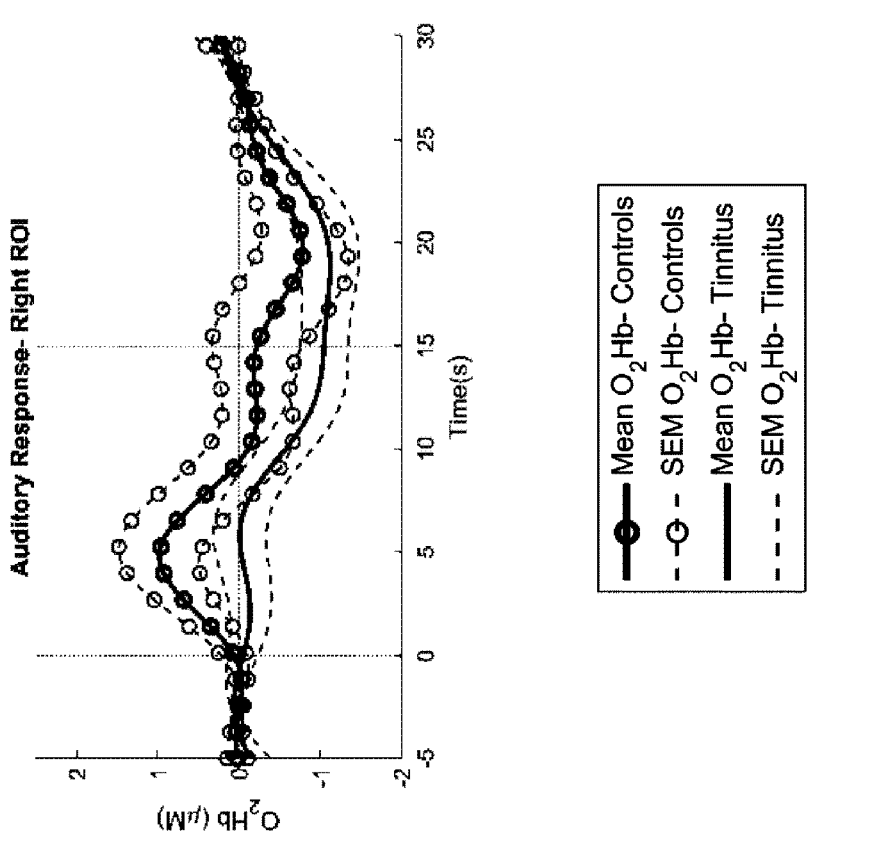
FIGS. 10A and 10B show group averaged $O_2Hb$ and HHb auditory and visual evoked responses, respectively, averaged over auditory and visual regions of interest.
Figure 10A:
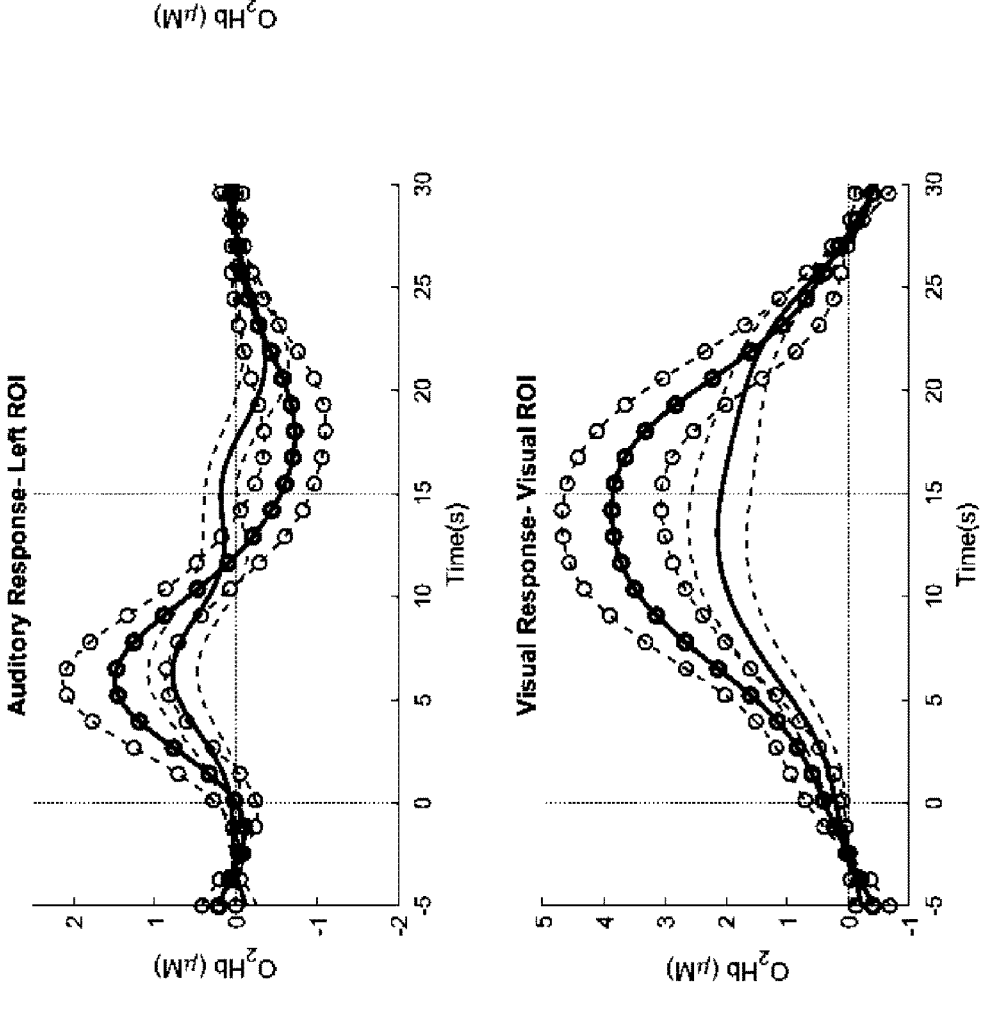
Figure 10B:
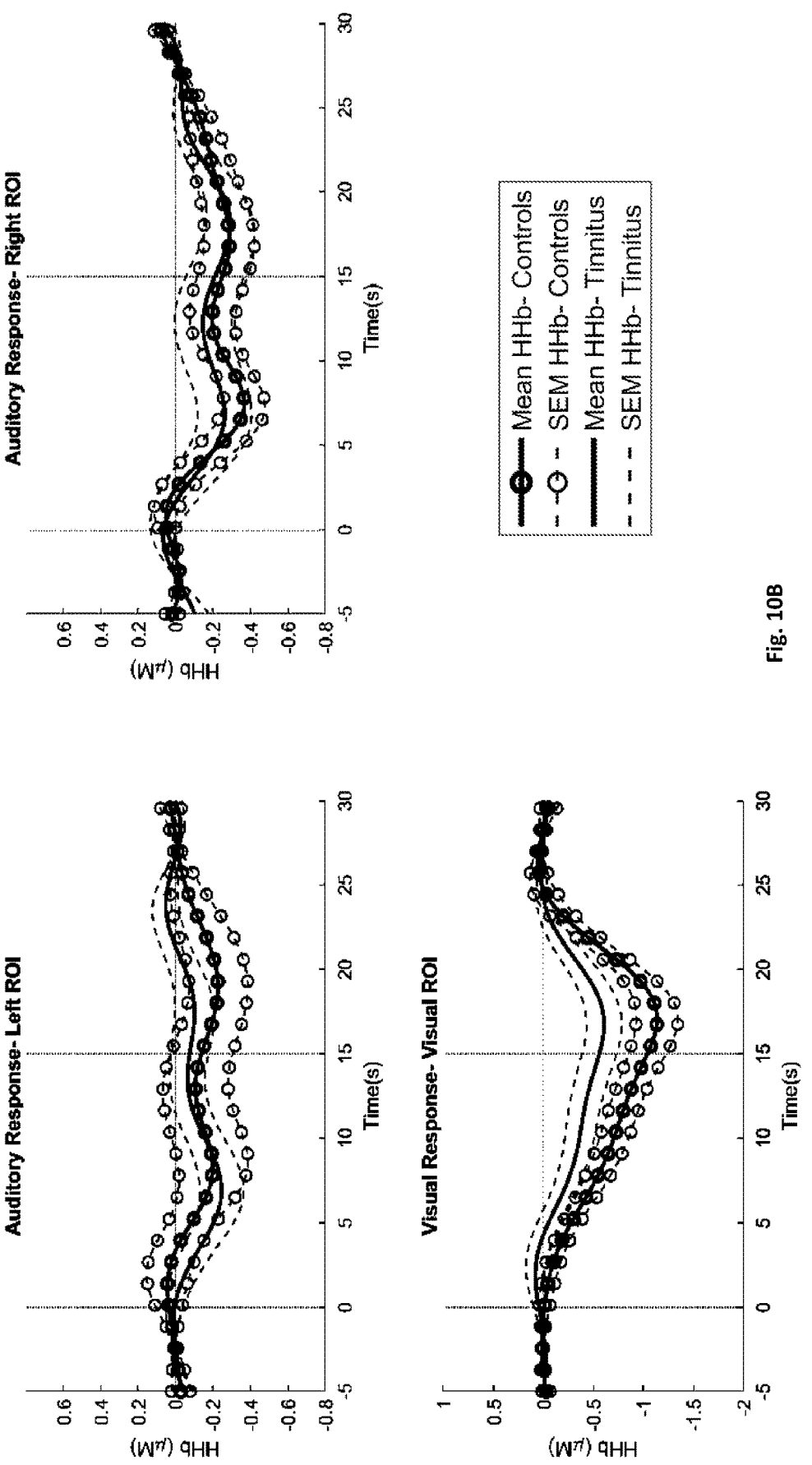

FIGS. 10A and 10B shows group averaged $O_2Hb$ and HHb auditory and visual responses, respectively, averaged over auditory and visual regions of interest (ROI). The dotted lines show standard error of mean (SEM). The dotted vertical lines show stimulus onset and offset times at 0 and 15 seconds. This figure allows visual comparison of the waveforms averaged over the auditory and visual channels. Auditory responses showed a clear onset or rise lasting around 5 seconds after stimulation. Visual responses were more sustained with a slower rise lasting around 15 seconds after stimulation.

Figure 11:
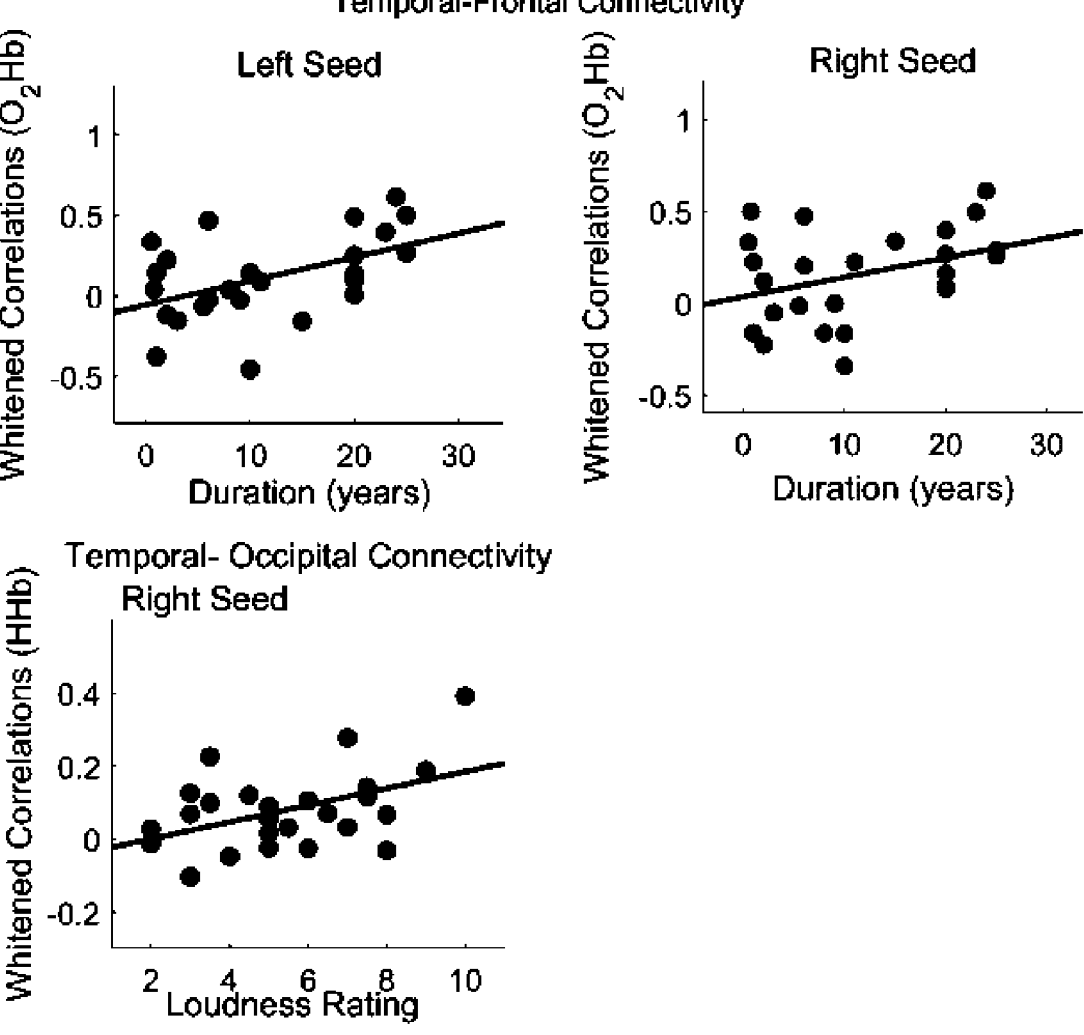
FIG. 11 shows the change in $O_2Hb$ derived temporal-frontal connectivity with duration of tinnitus (panel A) and the change in HHb derived temporal-occipital connectivity with subjective ratings of loudness (panel B)

Changes in fNIRS measures with tinnitus severity as assessed by the THI score, age, duration of tinnitus, hearing thresholds at 4 and 8 KHz and subjective ratings of loudness and annoyance were assessed using multiple linear regression. FIG. 11 shows the change in $O_2Hb$ derived temporal-frontal connectivity with duration of tinnitus (panel A) and the change in HHb derived temporal-occipital connectivity with subjective ratings of loudness (panel B). O₂Hb-derived connectivity between left and right seeds and frontal channels increased with duration of tinnitus with the correlation on the right side approaching significance. HHb-derived connectivity between the right seed and occipital channels increased significantly with subjective ratings of loudness.

Individual channel (rather than ROI averaged) auditory, visual and resting state fNIRS feature sets, either alone or in combination, were used with classifiers. Features were weighted (or ranked) by applying Information Gain as a feature extraction method. The results achieved using the various classifiers are shown in Table 2 below.

TABLE 2

Classifiers and features with highest accuracy for predicting subjects with tinnitus and controls

| Classifier | features | Sensitivity | Specificity | Accuracy |
|---|---|---|---|---|
| Naïve Bayes | Auditory response | 72.33% | 64.25% | 78.3% |
| Rule Induction | Combined auditory, visual and connectivity | 80.66% | 67.33% | 75.09% |
| Naïve Bayes | Combined auditory, visual and connectivity | 86.42% | 61.25% | 74.75% |
| Neural Network | Combined auditory, visual and connectivity | 71.41% | 74.62% | 72.33% |

A single feature set, auditory only, weighted above 0.45, with a Naïve Bayes classifier was able to separate tinnitus subjects from controls with an accuracy of 78.3% (Table 3). The weighting criterion resulted in 36 auditory features being used (20 O₂Hb and 16 HHb derived auditory response amplitudes). Combining auditory, visual and resting state features weighted above 0.56 and using Rule Induction, Naïve Bayes and Neural Networks classifiers also resulted in accuracies above 70%. Features used included 19 auditory, 17 visual and 22 resting state connectivity measures. Of these total 58 features, 35 were derived from O₂Hb and 23 from HHb signals. Connectivity measures in the selected features contained more right-seed features than left, and more temporal-occipital features compared to temporal-frontal ones. The highest accuracy for classifying tinnitus subjects from controls was achieved using Naïve Bayes classifier with auditory features. The highest sensitivity was achieved using Naïve Bayes classifier with features from all three conditions selected using Information Gain. The Artificial Neural Network algorithm resulted in similar sensitivity and specificity values of 71.41% and 74.62% respectively. KNN was also used to classify tinnitus subjects from controls. However, this resulted in a lower accuracy (~60%).

Table 4 shows classification results for differentiating slight/mild (n=18) from moderate/severe (n=7) tinnitus. To categorise these tinnitus subjects, the highest accuracies (above 75%) were achieved using connectivity measures weighted above 0.45, with Neural Network, KNN and Rule Induction classifiers (Table 4). A total of 48 features (23 O₂Hb and 25 HHb derived auditory response amplitudes) were included with most features from right-seed HHb temporal-frontal and temporal occipital measures. Highest sensitivity (correctly predicting those with moderate/severe tinnitus) and accuracy was achieved using the Neural Network classifier although low specificity of 51.23% was obtained.

TABLE 3

Classifiers and features with highest accuracy for predicting severity of tinnitus (slight/mild n = 18, versus moderate/severe n = 7) as rated using the Tinnitus Handicap Inventory (THI).

| Classifier | features | Sensitivity | Specificity | Accuracy |
|---|---|---|---|---|
| Neural network | Connectivity features | 51.23% | 95.12% | 87.32% |
| KNN(K = 1) | Connectivity features | 50.86% | 90.21% | 81.22% |
| Rule Induction | Connectivity features | 34.63% | 90.06% | 76.53% |

This study demonstrates that fNIRS can be used to differentiate subjects suffering from tinnitus from controls and identifies fNIRS features that are associated with subjective ratings of tinnitus severity. Further, the results of this study suggest that tinnitus characteristics such as loudness and annoyance may be measured independently using fNIRS.

Further testing increased the number of subjects to fifty-two subjects with chronic subjective tinnitus and thirty-one healthy adults with no history of tinnitus, neurological or hearing disorders. The patient demographics for the updated study are shown below in Table 4. The patients were matched for age and level of hearing.

TABLE 4

Patient demographics of increased subject pool

| | Mean (SEM) | |
| | Controls | Tinnitus |
|---|---|---|
| Age | 49.6 (2.8) | 53.4 (1.7) |
| Average hearing (left) | 15 (1.8) | 18.7 (1.2) |
| Average hearing (right) | 13.2 (1.7) | 17.1 (1.3) |

Figure 14:
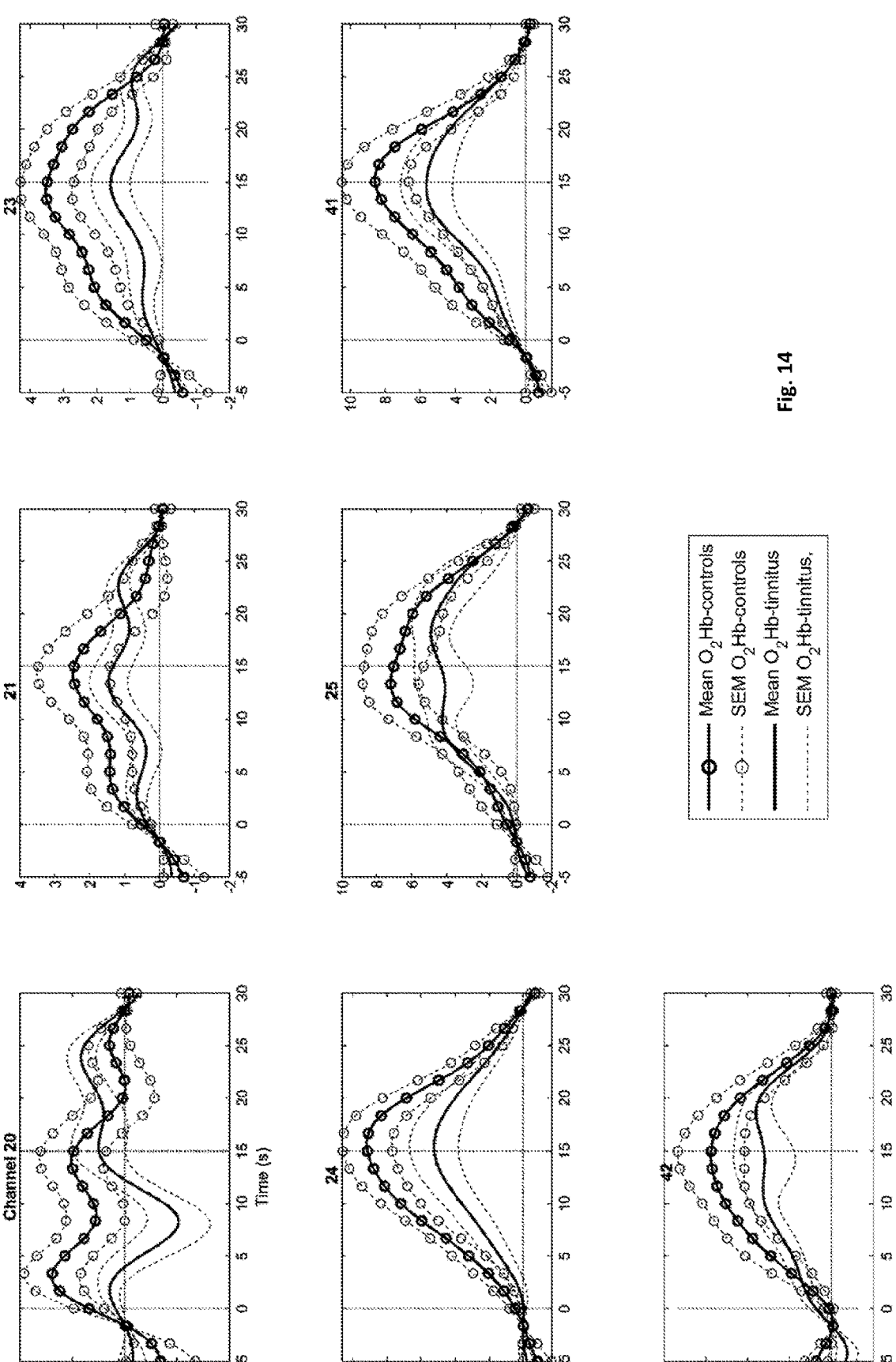
FIG. 14 shows $O_2Hb$ visual evoked responses recorded from occipital channels over the cuneus and superior occipital gyrus.

FIG. 14 shows O₂Hb visual evoked response data recorded from occipital channels over the cuneus and superior occipital gyrus with this enlarged subject group. The channel numbers are shown above each graph. Vertical lines show stimulus onset and offset times at 0 and 15 seconds. The visual response was more sustained in duration following stimulus onset compared to the auditory response. Response amplitudes averaged over 10-15 seconds following stimulus onset were significantly larger in the control group. From this data, the channels in the visual region that best differentiated tinnitus patients from controls were channels 24, 25, 41 and 42.

Figure 15A:
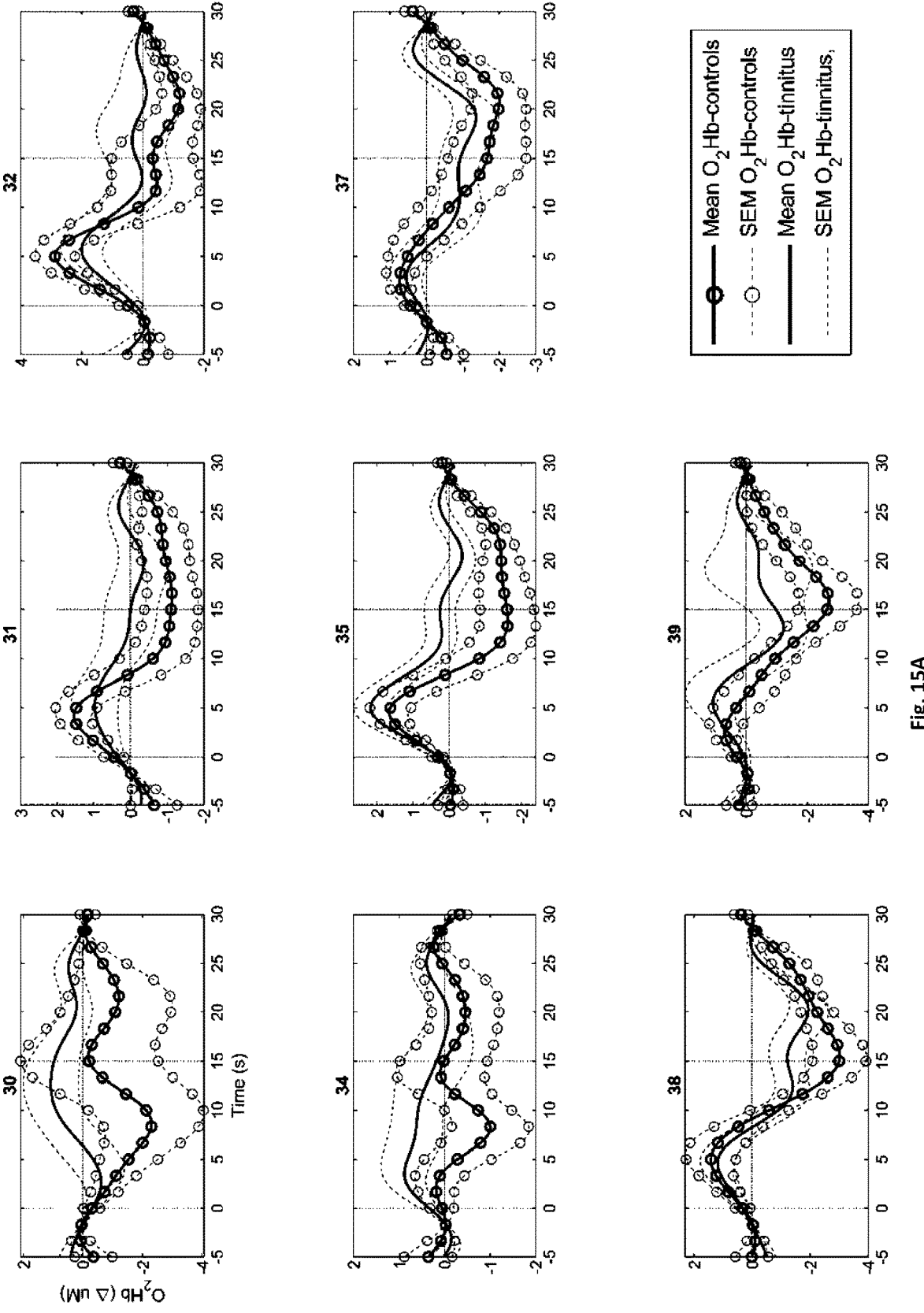
FIGS. 15A and 15B show group averaged HHb fNIRS auditory evoked responses recorded from channels over the left and right temporal cortex, respectively.
Figure 15B:
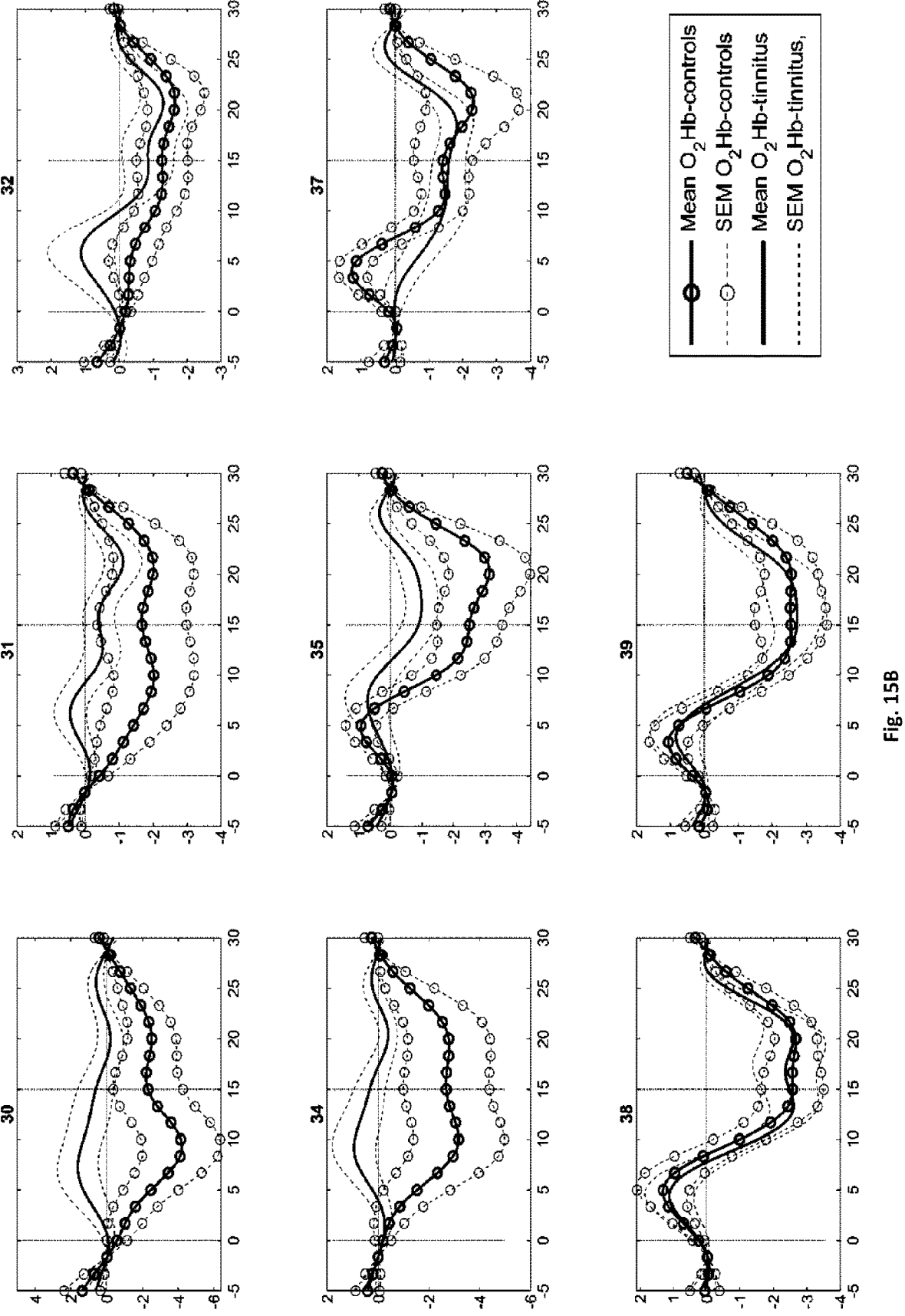

FIGS. 15A and 15B show auditory response data from the left and right temporal region, respectively, from the enlarged subject group. The channel numbers are shown above each graph. Vertical lines show stimulus onset and offset times at 0 and 15 seconds. In the left temporal region, channels 10, 11, 14, 16, 17 and 18 showed significant differences between the tinnitus patients and controls. Of these, channels 10 and 11, 14 and 16, and 17 and 18 showed similar differences. It may be that only one of each of these pairs of channels is required. The same pairing of channels (or regions of interest in the brain) could be used in the right temporal region. However, in the right temporal region, channels 35 and 37 showed the most significant differences between groups. This difference between the left temporal region and the right temporal region may be due to asymmetry in brain activity commonly found in tinnitus patients.

Example 2

A cochlear implant (CI) is a device that is used to provide a sense of sound to a person who is deaf and, in some cases, may also suppress tinnitus. However, the mechanisms of action of cochlear implants on tinnitus are unclear. Worsening of tinnitus after implantation has been reported in 4-26% of cases.

A study was conducted on 10 cochlear implant users who experience tinnitus and whose perception of tinnitus (i.e. loudness and annoyance perceived) is altered with use of their implant. Resting state data was recorded with the implant switched on and off. Evoked response data in response to 15-second visual stimuli was recorded with the implant switched on and off. Auditory responses were not included in this protocol as they cannot be recorded with the implant switched off.

Figure 12:
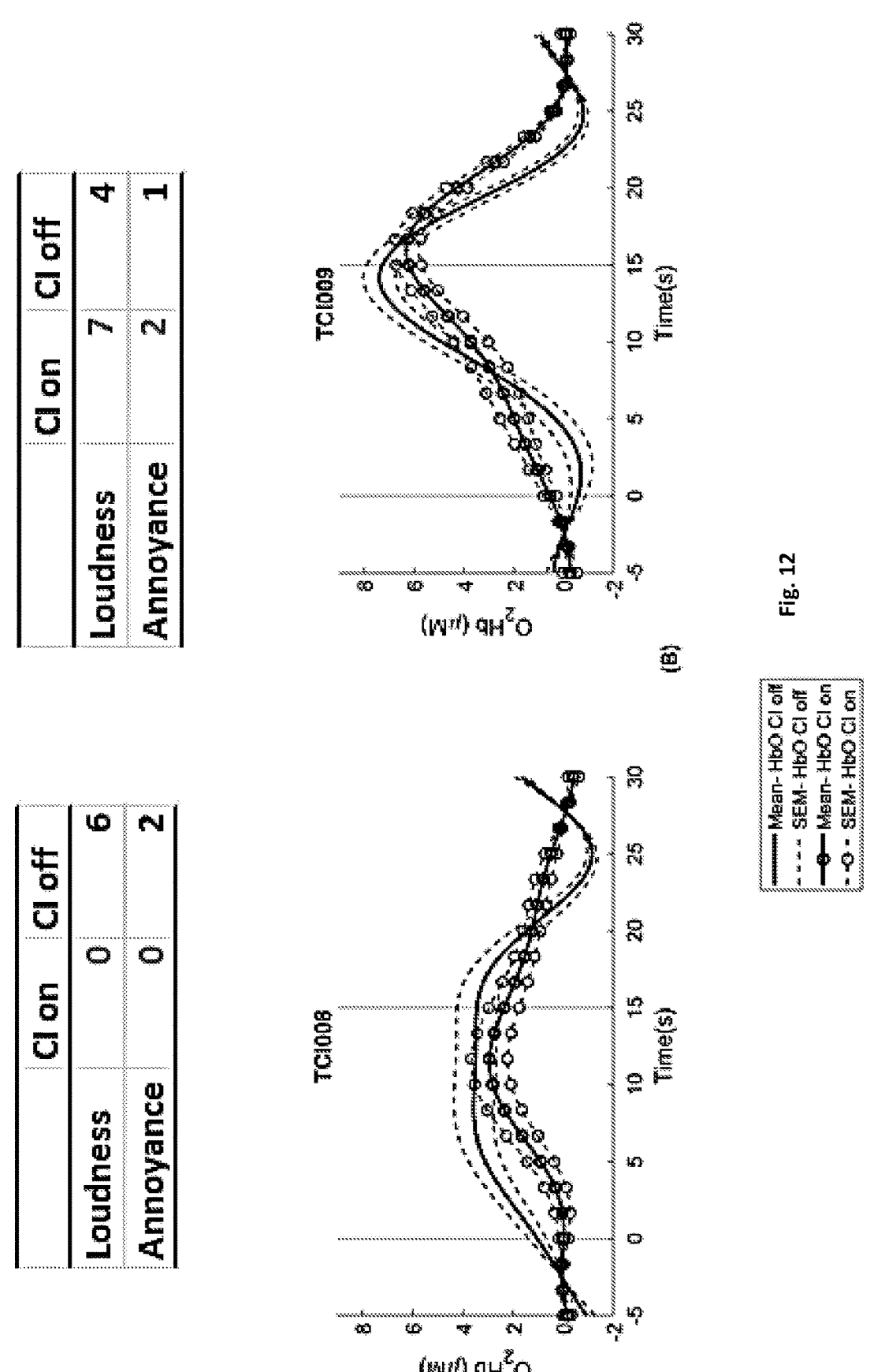
FIG. 12 shows representative visual evoked responses to 15-second visual stimuli from two cochlear implant users, with their implant switched on and switched off.

FIG. 12 shows representative visual evoked responses to 15-second visual stimuli from two cochlear implant users, with their implant switched on and switched off. Mean (solid lines) and standard error of mean (dashed lines) of 10 averaged responses are shown for each person. The first subject (TCI008, represented in panel A) reported their tinnitus was completely suppressed with use of their implant. The second subject (TCI009, represented in panel B) experienced the opposite effect, with their tinnitus becoming louder with use of their implant. This opposing effect is reflected in the onset (t=0-5 s) of the visual response. When the cochlear implant suppresses tinnitus (TCI008), the onset response amplitude with the implant switched on (gray trace) is smaller than with the implant switched off (black trace). Within that onset period, the opposite is found when cochlear implantation makes tinnitus worse (TCI009).

A comparison of the resting state recordings obtained with the cochlear implant switched on and off demonstrated that data from fNIRS signals with a cochlear implant switched off may be predictive of whether an active cochlear implant is likely to be effective in alleviating tinnitus symptoms.

Figure 13:
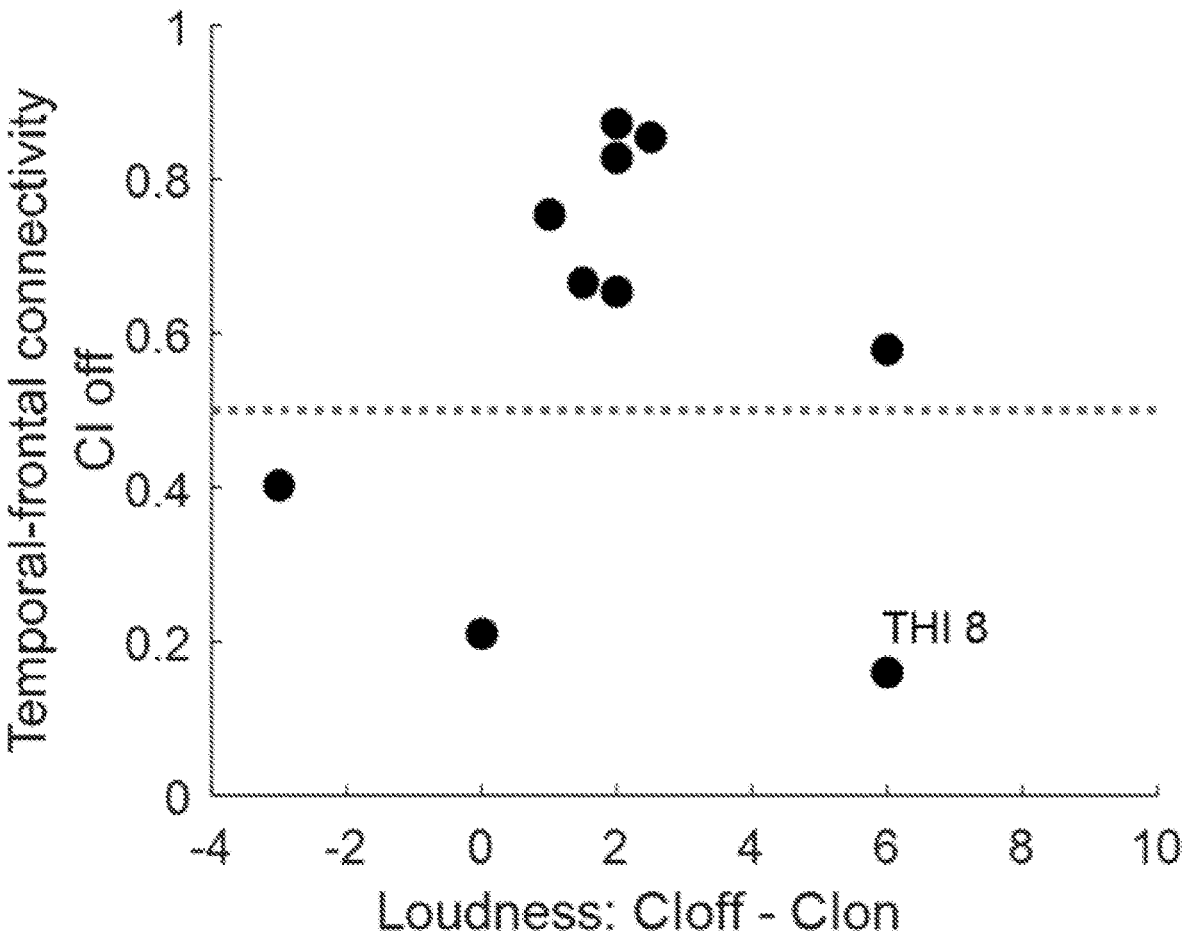
FIG. 13 shows right seed temporal-frontal connectivity with a cochlear implant switched off plotted against change in loudness perception with the cochlear implant switched on and off.

FIG. 13 shows right seed temporal-frontal connectivity with the subject's cochlear implant switched off versus change in loudness perception with the cochlear implant switched on and off. Positive numbers on the x-axis refer to a reduction in loudness perception with the CI turned on. Resting state functional connectivity measures above 0.5 are associated with a decrease in tinnitus loudness when the implant is switched on. In this study, one individual with a connectivity value below 0.5 experienced a decrease in tinnitus loudness with use of their implant. However, for this individual, the severity of their tinnitus as measured by the Tinnitus Handicap Inventory was low (THI:8), making it unlikely that a cochlear implant would be considered as a treatment.

Based on these findings, fNIRS signals recorded prior to receiving an implant may provide a suitable prognostic measure of the likely effectiveness of the a cochlear implant in suppressing tinnitus.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A method for characterising tinnitus in a subject using functional near-infrared spectroscopy (fNIRS), the method comprising:

receiving data at a processor device, the received data comprising fNIRS signals indicative of cortical activity in one or more regions of the subject's brain; and processing the received data using the processor device, the processing comprising:

inputting, into a model, one or more feature values including one or more features of the received data, wherein the model is configured to provide one or more classification results based on the one or more feature values, the one or more classification results being indicative of at least one characteristic of tinnitus in the subject, wherein the received data comprises evoked response data comprising fNIRS signals indicative of cortical activity in at least one region of the subject's brain resulting from a plurality of discrete stimuli delivered to the subject in sequence, wherein the sequence includes one or more non-stimulus interval periods, wherein the one or more feature values include one or more features of the evoked response data, and wherein the plurality of discrete stimuli comprises at least one of a plurality of discrete auditory stimuli and a plurality of discrete visual stimuli.

2. The method of claim 1, wherein the classification results include one or more of: a presence or absence of tinnitus in the subject; a severity rating of tinnitus in the subject; quantification of loudness of the tinnitus; and quantification of annoyance produced by the tinnitus.

3. The method of claim 1, wherein the model comprises a trained model, and wherein the model has been trained with an artificial intelligence (AI) algorithm based on a previous one or more feature values mapped to subjective measures of characteristics of tinnitus.

4. The method of claim 3, wherein the model provides classification results using a classification algorithm selected from the group including: Naïve Bayes; K-nearest neighbour (KNN); Rule Induction; Artificial Neural Networks (ANN), and multi-level hierarchical classification.

5. The method of claim 1, further comprising applying a therapy for treating tinnitus and, through the processing of the received data, detecting a change in the one or more characteristics of the tinnitus as a result of applying the therapy.

6. The method of claim 1, comprising determining a quality of each fNIRS signal and removing signals of inadequate quality prior to processing of the received data.

7. The method of claim 1, wherein the fNIRS signals comprise signals indicative of changes in oxyhaemoglobin ($O_2Hb$) concentration in the subject's brain and/or signals indicative of changes in deoxyhaemoglobin (HHb) concentration in the subject's brain.

8. The method of claim 1, wherein the received data comprises:

resting-state data comprising fNIRS signals indicative of cortical activity in two or more regions of the subject's brain while the subject is at rest, and wherein processing the data further comprises determining at least one resting-state functional connectivity measure between the at least two regions of the subject's brain based on the resting-state data, and wherein the one or more feature values include one or more features of the at least one resting-state functional connectivity measure.

9. The method of claim 1, wherein the model is configured to provide a prognostic measure indicative of whether a proposed therapy for treating tinnitus in the subject is likely to be effective.

10. The method of claim 9, wherein a quality of each fNIRS signal is determined based on one or more of a level of signal gain and a level of cardiac signal content.

11. A non-transitory machine readable storage medium comprising instructions configured to cause a processor device to execute the method of claim 1.

12. A system for characterising tinnitus in a subject using functional near infrared spectroscopy (fNIRS), the system comprising:

a processor device, configured to:

receive data, the received data comprising fNIRS signals indicative of cortical activity in one or more regions of the subject's brain; and process the received data, wherein the processing comprises:

inputting, into a model, one or more feature values including one or more features of the received data, wherein the model is configured to provide one or more classification results based on the one or more feature values, the one or more classification results being indicative of at least one characteristic of tinnitus in the subject, wherein the received data comprises evoked response data comprising fNIRS signals indicative of cortical activity in at least one region of the subject's brain resulting from a plurality of discrete stimuli delivered to the subject in sequence, wherein the sequence includes one or more non-stimulus interval periods, wherein the one or more feature values include one or more features of the evoked response data, and wherein the plurality of discrete stimuli comprises at least one of a plurality of discrete auditory stimuli and a plurality of discrete visual stimuli.

13. The system of claim 12, wherein the received data comprises:

resting-state data comprising fNIRS signals indicative of cortical activity in two or more regions of the subject's brain while the subject is at rest, and wherein processing the data further comprises determining at least one resting-state functional connectivity measure between the at least two regions of the subject's brain based on the resting-state data, and wherein the one or more feature values include one or more features of the at least one resting-state functional connectivity measure.

14. The system of claim 12, further comprising:

a fNIRS system configured to measure a level of cortical activity in at least two regions of the subject's brain.

15. The system of claim 12, the system further comprising an auditory stimulator configured to deliver the auditory stimulus to the subject and/or a visual stimulator configured to deliver the visual stimulus to the subject.

16. The system of claim 12, wherein the fNIRS system comprises a multi-channel fNIRS system, wherein each channel is defined by a source-detector pair.

17. The system of claim 16 comprising one or more channels configured to be positioned over each of the frontal, left and right temporal and occipital regions of the subject's brain.

\* \* \* \* \*